(12) United States Patent
Chance

(10) Patent No.: US 7,610,082 B2
(45) Date of Patent: *Oct. 27, 2009

(54) OPTICAL SYSTEM AND METHOD FOR IN-VIVO TRANSCRANIAL EXAMINATION OF BRAIN TISSUE OF A SUBJECT

(75) Inventor: Britton Chance, Marathon, FL (US)

(73) Assignee: Non-Invasive Technology, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/982,542

(22) Filed: Nov. 5, 2004

(65) Prior Publication Data

US 2005/0228291 A1   Oct. 13, 2005

Related U.S. Application Data

(63) Continuation of application No. 09/622,112, filed as application No. PCT/US99/03030 on Feb. 11, 1999, now abandoned.

(60) Provisional application No. 60/074,296, filed on Feb. 11, 1998, provisional application No. 60/098,018, filed on Aug. 26, 1998.

(51) Int. Cl.
*A61B 5/00* (2006.01)
(52) U.S. Cl. .............. 600/475; 600/323; 600/328; 600/329; 600/340; 600/431; 600/477; 600/479
(58) Field of Classification Search ............ 600/310, 600/322–324, 326, 328, 329, 340, 431, 473, 600/475–477, 479
See application file for complete search history.

(56) References Cited

U.S. PATENT DOCUMENTS 2,706,927 A    4/1955   Wood (Continued)

FOREIGN PATENT DOCUMENTS

DE    25 38 985    5/1976

(Continued)

OTHER PUBLICATIONS

PCT International Search Report, Int'l Appln. No. PCT/US97/16309, mailed Feb. 10, 1998, 9 pp.

(Continued)

*Primary Examiner*—Ruth S Smith
(74) *Attorney, Agent, or Firm*—Ian David Zitkovsky

(57) ABSTRACT

An optical examination technique employs an optical system for in vivo non-invasive transcranial examination of brain tissue of a subject. The optical system includes an optical module arranged for placement on the exterior of the head, a controller and a processor. The optical module includes an array of optical input ports and optical detection ports located in a selected geometrical pattern to provide a multiplicity of photon migration paths inside the biological tissue. Each optical input port is constructed to introduce into the examined tissue visible or infrared light emitted from a light source. Each optical detection port is constructed to provide light from the tissue to a light detector. The controller is constructed and arranged to activate one or several light sources and light detectors so that the light detector detects light that has migrated over at least one of the photon migration paths. The processor receives signals corresponding to the detected light and forms at least two data sets, a first of said data sets representing blood volume in the examined tissue region and a second of said data sets representing blood oxygenation of the examined tissue. The processor is arranged to correlate the first and second data sets to detect abnormal tissue in the examined tissue.

37 Claims, 22 Drawing Sheets

U.S. PATENT DOCUMENTS

| | | | |
|---|---|---|---|
| 2,790,438 A | 4/1957 | Taplin et al. |
| 3,068,742 A | 12/1962 | Hicks, Jr. et al. |
| 3,412,729 A | 11/1968 | Smith, Jr. |
| 3,461,856 A | 8/1969 | Polanyi |
| 3,638,640 A | 2/1972 | Shaw |
| 3,704,706 A | 12/1972 | Herczfeld et al. |
| 3,709,612 A | 1/1973 | Clemens |
| 3,866,599 A | 2/1975 | Johnson |
| 3,994,585 A | 11/1976 | Frey |
| 3,998,550 A | 12/1976 | Konishi et al. |
| 4,014,321 A | 3/1977 | March |
| 4,029,085 A | 6/1977 | DeWitt et al. |
| 4,086,915 A | 5/1978 | Kofsky et al. |
| 4,119,406 A | 10/1978 | Clemens |
| 4,129,125 A | 12/1978 | Lester et al. |
| 4,138,727 A | 2/1979 | Mantz |
| 4,162,405 A | 7/1979 | Chance et al. |
| 4,167,331 A | 9/1979 | Nielsen |
| 4,222,389 A | 9/1980 | Rubens |
| 4,223,680 A | 9/1980 | Jöbsis |
| 4,224,948 A | 9/1980 | Cramer et al. |
| 4,259,963 A | 4/1981 | Huch |
| 4,266,554 A | 5/1981 | Hamaguri |
| 4,281,645 A | 8/1981 | Jöbsis |
| 4,321,930 A | 3/1982 | Jöbsis et al. |
| 4,380,240 A | 4/1983 | Jöbsis et al. |
| 4,416,285 A | 11/1983 | Shaw et al. |
| 4,447,884 A | 5/1984 | Wada |
| 4,452,250 A | 6/1984 | Chance et al. |
| 4,469,107 A | 9/1984 | Asmar et al. |
| 4,510,938 A | 4/1985 | Jöbsis et al. |
| 4,515,165 A | 5/1985 | Carroll |
| 4,576,173 A | 3/1986 | Parker et al. |
| 4,612,938 A | 9/1986 | Dietrich et al. |
| 4,648,892 A | 3/1987 | Kittrell et al. |
| 4,655,225 A | 4/1987 | Dähne et al. |
| 4,700,708 A | 10/1987 | New, Jr. et al. |
| 4,714,341 A | 12/1987 | Hamaguri et al. |
| 4,738,267 A | 4/1988 | Lazorthes et al. |
| 4,773,422 A | 9/1988 | Isaacson et al. |
| 4,774,679 A | 9/1988 | Carlin |
| 4,800,495 A | 1/1989 | Smith |
| 4,800,885 A | 1/1989 | Johnson |
| 4,805,623 A | 2/1989 | Jöbsis |
| 4,807,637 A | 2/1989 | Bjorkholm |
| 4,824,242 A | 4/1989 | Frick et al. |
| 4,836,207 A | 6/1989 | Bursell et al. |
| 4,846,183 A | 7/1989 | Martin |
| 4,869,254 A | 9/1989 | Stone et al. |
| 4,880,304 A | 11/1989 | Jaeb et al. |
| 4,908,762 A | 3/1990 | Suzuki et al. |
| 4,926,867 A | 5/1990 | Kanda et al. |
| 4,937,526 A | 6/1990 | Ehman et al. |
| 4,940,453 A | 7/1990 | Cadwell |
| 4,951,682 A | 8/1990 | Petre |
| 4,972,331 A | 11/1990 | Chance |
| 5,035,243 A | 7/1991 | Muz |
| 5,057,695 A | 10/1991 | Hirao et al. |
| 5,062,431 A | 11/1991 | Potter |
| 5,088,493 A | 2/1992 | Giannini et al. |
| 5,090,415 A | 2/1992 | Yamashita et al. |
| 5,106,387 A | 4/1992 | Kittrell et al. |
| 5,119,815 A | 6/1992 | Chance |
| 5,122,974 A | 6/1992 | Chance |
| 5,137,355 A | 8/1992 | Barbour et al. |
| 5,139,025 A | 8/1992 | Lewis et al. |
| 5,143,081 A | 9/1992 | Young et al. |
| 5,158,090 A | 10/1992 | Waldman et al. |
| 5,174,298 A | 12/1992 | Dolfi et al. |
| 5,178,142 A | 1/1993 | Harjunmaa et al. |
| 5,187,672 A | 2/1993 | Chance et al. |
| 5,190,039 A | 3/1993 | Takeuchi et al. |
| 5,203,339 A | 4/1993 | Knüttel et al. |
| 5,213,105 A | 5/1993 | Gratton et al. |
| 5,218,962 A | 6/1993 | Mannheimer et al. |
| 5,257,202 A | 10/1993 | Feddersen et al. |
| 5,277,181 A | 1/1994 | Mendelson et al. |
| 5,287,276 A | 2/1994 | Crawford et al. |
| 5,300,097 A | 4/1994 | Lerner et al. |
| 5,309,907 A | 5/1994 | Fang et al. |
| 5,309,912 A | 5/1994 | Knüttel |
| 5,353,799 A | 10/1994 | Chance |
| 5,358,503 A | 10/1994 | Bertwell et al. |
| 5,402,778 A | 4/1995 | Chance |
| 5,408,093 A | 4/1995 | Ito et al. |
| 5,413,098 A | 5/1995 | Benaron |
| 5,416,582 A | 5/1995 | Knutson et al. |
| 5,431,170 A | 7/1995 | Mathews |
| 5,494,032 A | 2/1996 | Robinson et al. |
| 5,497,769 A | 3/1996 | Grattoo et al. |
| 5,551,422 A | 9/1996 | Simonsen et al. |
| 5,551,423 A | 9/1996 | Sugiura |
| 5,564,417 A | 10/1996 | Chance |
| 5,596,987 A | 1/1997 | Chance |
| 5,625,458 A | 4/1997 | Alfano et al. |
| 5,655,530 A | 8/1997 | Messerschmidt |
| 5,673,701 A | 10/1997 | Chance |
| 5,706,821 A | 1/1998 | Matcher et al. |
| 5,779,631 A | 7/1998 | Chance |
| 5,782,755 A | 7/1998 | Chance et al. |
| 5,807,263 A | 9/1998 | Chance |
| 5,845,639 A | 12/1998 | Hochman et al. |
| 5,853,370 A | 12/1998 | Chance et al. |
| 5,943,133 A | 8/1999 | Zeylikovich et al. |
| 5,949,077 A | 9/1999 | Alfano et al. |
| 5,983,125 A | 11/1999 | Alfano et al. |
| 5,987,351 A | 11/1999 | Chance |
| 6,006,001 A | 12/1999 | Alfano et al. |
| 6,058,324 A | 5/2000 | Chance |
| 6,091,983 A | 7/2000 | Alfano et al. |
| 6,108,576 A | 8/2000 | Alfano et al. |
| 6,215,587 B1 | 4/2001 | Alfano et al. |

FOREIGN PATENT DOCUMENTS

| | | |
|---|---|---|
| DE | 31 00610 C2 | 1/1981 |
| DE | 208 297 | 6/1982 |
| DE | 43 03 047 A | 8/1994 |
| EP | 0 099 756 | 1/1984 |
| EP | 0 102 816 | 3/1984 |
| EP | 0 290 279 | 9/1985 |
| EP | 0 196 396 | 10/1986 |
| EP | 0 282 234 | 12/1987 |
| EP | 0 488 565 A1 | 6/1992 |
| GB | 2 068 537 | 8/1981 |
| GB | 2228314 | 8/1990 |
| JP | 59-1688.34 | 9/1984 |
| JP | 63-61923 | 3/1988 |
| JP | 63-148307 | 9/1988 |
| JP | 61-60903 | 4/1996 |
| WO | WO 84/04665 | 12/1984 |
| WO | WO 88/01485 | 3/1988 |
| WO | WO 90/09003 | 8/1990 |
| WO | WO 92/13598 | 8/1992 |
| WO | WO 92/20273 | 11/1992 |
| WO | WO 93/05686 | 12/1993 |
| WO | WO 94/16615 | 4/1994 |
| WO | WO 95/02987 | 2/1995 |
| WO | WO 93/25145 | 12/1995 |
| WO | WO 96/20638 | 7/1996 |

| | | |
|---|---|---|
| WO | WO97/20494 | 12/1997 |

OTHER PUBLICATIONS

Apicella et al., "Fast multi-modality image matching", SPIE, vol. 1092, pp. 252-263, 1989.

Arridge, "The Forward and Inverse Problems in Time Resolved Infra-Red Imaging", Medical Optical Tomography: Functional Imaging and Monitoring, SPIE Optical Engineering Press, vol. IS11, pp. 35-64, 1993.

Arridge et al., "Reconstruction Methods for Infra-red Absorption Imaging", SPIE, vol. 1431, pp. 204-215, 1991.

Barlow et al., "Breast Biopsy Analysis By Spectroscopic Imaging", Photon Migration in Tissues, Plenum Press, New York, pp. 111-119, 1989.

Benaron et al., "A Medical Perspective at the Threshold of Clinical Optical Tomography", Medical Optical Tomography: Functional Imaging and Monitoring. SPIE Optical Engineering Press, vol. IS11, pp. 3-9, 1993.

Bonner et al., "Model for photon migration in turbid biological media", J. Opt. Soc. Am. A., vol. 4, No. 3, pp. 423-427, 1987.

Chance, "The Future of Time Resolved Spectroscopy and Imaging", Proceedings of The Third International Conference: Peace through Mind/Brain Science, pp. 166-172, Aug. 5-10, 1990, Hamamatsu, Japan.

Chance et al., "Time Resolved Spectroscopy of Hemoglobin and Myoglobin in Resting and Ischemic Muscle", Anal. Biochem. 174:698-707, 1988.

Chance et al., "Photon Migration in Muscle and Brain", Photon Migration in Tissues, Plenum Press, New York, pp. 121-135, 1989.

Chance et al., "Rapid and Sensitive Spectrophotometry. I. The Accelerated and Stopped-Flow Methods for the Measurement of the Reaction Kinetics and Spectra of Unstable-Compounds in the Visible Region of the Spectrum", The Review of Scientific Instruments, vol. 22, pp. 619-627, 1951.

Chance et al., "Rapid and Sensitive Spectrophotometry. II. A Stopped-Flow Attachment for a Stabilized Quartz Spectrophotometer", The Review of Scientific Instruments, vol. 22, pp. 627-638, 1951.

Chance et al., "Comparison of time-resolved and -unresolved measurements of deoxyhemoglobin in brain", Proc. Natl. Acad. Sci. USA., vol. 85, pp. 4971-4975, 1988.

Colak et al., "Optical BackProjection Tomography in Heterogeneous Diffusive Media", Advances in Optical Imaging and Photon Migration, TOPS, vol. 2, pp. 282-289, 1996.

Cui et al., "Experimental Study of Migration Depth for the Photons Measured At Sample Surface", SPIE, vol. 1431, pp. 180-191, 1991.

Feng et al., "Analytical perturbation theory of photon migration in the presence of a single absorbing or scattering defect sphere", SPIE, vol. 2389, pp. 54-63, 1995.

Fishkin et al., "Diffusion of Intensity Modulated Near-Infrared Light in Turbid Media", SPIE, vol. 1431, pp. 122-135, 1991.

Gratton et al., "The Possibility of a Near Infrared Optical Imaging System Using Frequency Domain Methods", Mind Brain Imaging Program, Aug. 5-10, 1990, Hamamatsu, Japan.

Grünbaum et al., "Diffuse Tomography", SPIE, vol. 1431, pp. 232-238, 1991.

Greenfeld, "A Tissue Model for Investigating Photon Migration in Trans-Cranial Infrared Imaging", Photon Migration in Tissues, Plenum Press (New York), pp. 147-168, 1989.

Grinvald et al., "Functional Architecture of Cortex Revealed by Optical Imaging of Intrinsic Signals", Nature, 324:361-364, 1986.

Haida et al., "A Method to Estimate the Ratio of Absorption Coefficients of Two Wavelengths Using Phase Modulated NIR Spectroscopy", abstract submitted to ISOTT in Mainz, Germany, 1992.

Haida et al., "A Method to Estimate the Ratio of Absorption Coefficients of Two Wavelengths Using Phase Modulated Near Infrared Light Spectroscopy", Oxygen Transport to Tissue XV, Plenum Press, New York, vol. 345, pp. 829-835, 1994.

Haida et al., "A Method to Estimate the Ratio of Absorption Coefficients of Two Wavelengths Using Phase-Modulated Near Infrared Light Spectroscopy", Analytical Biochemistry, vol. 208, pp. 348-351, 1993.

Hajnal et al., "Artifacts Due to Stimulus Correlated Motion in Functional Imaging of the Brain", MRM, pp. 283-291, 1994.

Hoshi et al., "Detection of dynamic changes in cerebral oxygenation coupled to neuronal function during mental work in man", Neuroscience Letters, vol. 150, pp. 5-8, 1993.

Maki et al., "Spatial and temporal analysis of human motor activity using noninvasive NIR topography", Med. Phys., vol. 22, No. 12, pp. 1997-2005, 1995.

Matcher et al., "Absolute quantification methods in tissue near infrared spectroscopy", SPIE, vol. 2389, pp. 486-495, 1995.

Nioka et al., "Optical Imaging of Breast Tumors with various methods", Oxygen Transport to Tissue, vol. XVIII, pp. 227-232, 1997.

Oda et al., "Non-Invasive Hemoglobin Oxygenation Monitor and Computered Tomography by NIR Spectrophotometry", SPIE 1431:284-293, 1991.

Ogawa et al., "The Sensitivity of Magnetic Resonance Image Signals of a Rat Brain to Changes in the Cerebral Venous Blood Oxygenation", MRM, vol. 29, pp. 205-210, 1993.

Pelizzari et al., "Accurate Three-Dimensional Registration of CT, PET, and/or MR Images of the Brain", J. Computer-Assisted Tomography, vol. 13, No. 1, pp. 20-26, 1989.

Polishchuk et al., "Non-Euclidean diffusion and 'Format' photons in turbid media", SPIE, vol. 2389, pp. 6-9, 1995.

Sevick et al., "The physical basis of biomedical optical imaging using time-dependent measurements of photon migration in the frequency domain", Medical Optical Tomography: Functional Imaging and Monitoring, SPIE Optical Engineering Press, vol. IS11, pp. 483-512, 1993.

Sevick et al., "Analysis of Absorption, Scattering and Hemoglobin Saturation Using Phase Modulation Spectroscopy", SPIE vol. 1431, pp. 264-275, 1991.

Sevick et al., "Photon Migration in a Model of the Head Measured Using Time- and Frequency- Domain Techniques Potentials of Spectroscopy and Imaging", SPIE, vol. 1431, pp. 84-96, 1991.

Sevick et al., "Quantitation of Time-and Frequency-Resolved Optical Spectra for the Determination of Tissue Oxygenation," Analytical Biochemistry, vol. 195, pp. 330-351, 1991.

Singer et al., "Image Reconstruction of the Interior of Bodies that Diffuse Radiation", Science, vol. 248, pp. 990-993, 1990.

Weng et al., "Measurement of Biological Tissue Metabolism Using Phase Modulation Spectroscopy Technology," SPIE, 1431:161-171, 1991.

Woods et al., "Rapid Automated Algorithm for Aligning and Reslicing PET Images", J. Computer Assisted Tomography, vol. 16, No. 4, pp. 620-633, 1992.

Yamashita et al., "The Neonate Brain (NIR) and Breast Imaging Using Transillumination", Photon Migration in Tissues, Plenum Press, New York, pp. 55-67, 1989.

Brochure, Becton Dickinson, Cardio-Green® (CG®) HW&D Brand of Sterile Indocyanine Green, USP, Apr. 1981.

"Watching The Brain At Work", IEEE, Spectrum, vol. 20, No. 3, pp. 52-57, 1983.

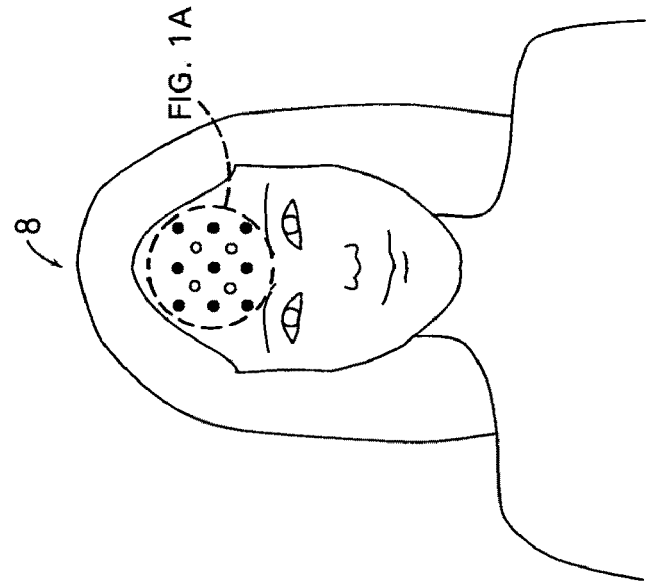
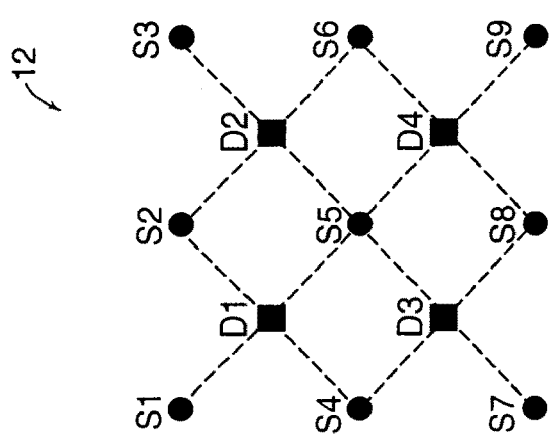
FIG. 1
FIG. 1A

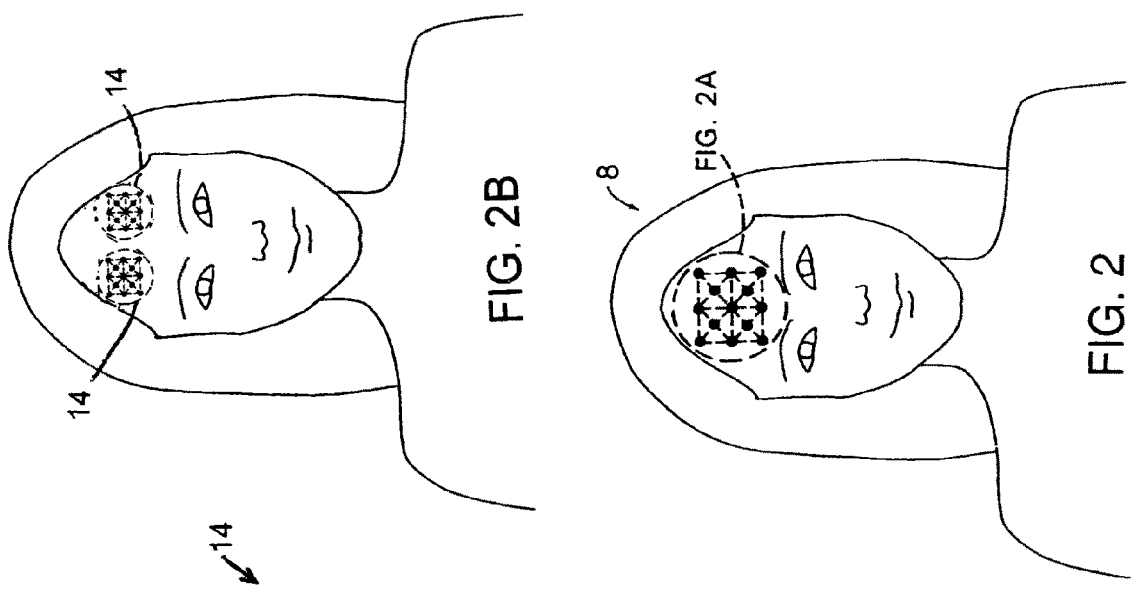
FIG. 2B
FIG. 2
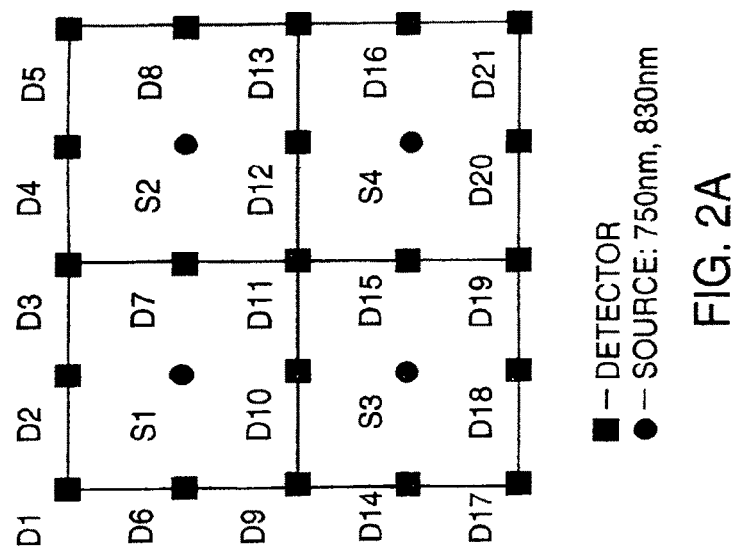
FIG. 2A
■ – DETECTOR
● – SOURCE: 750nm, 830nm

| SOURCES | DETECTORS |
|---|---|
| 1, 2, 1a AND 2a | 1 |
| 2, 3, 2a, AND 3a | 2 |
| 4, 5, 4a, AND 5a | 1 |
| 5, 6, 5a, AND 4a | 2 |
| 7, 8, 7a, AND 8a | 3 |
| 8, 9, 8a, AND 9a | 4 |
| 4, 5, 4a, AND 5a | 3 |
| 5, 6, 5a, AND 6a | 4 |
| 7, 8, 7a, AND 8a | 3 |

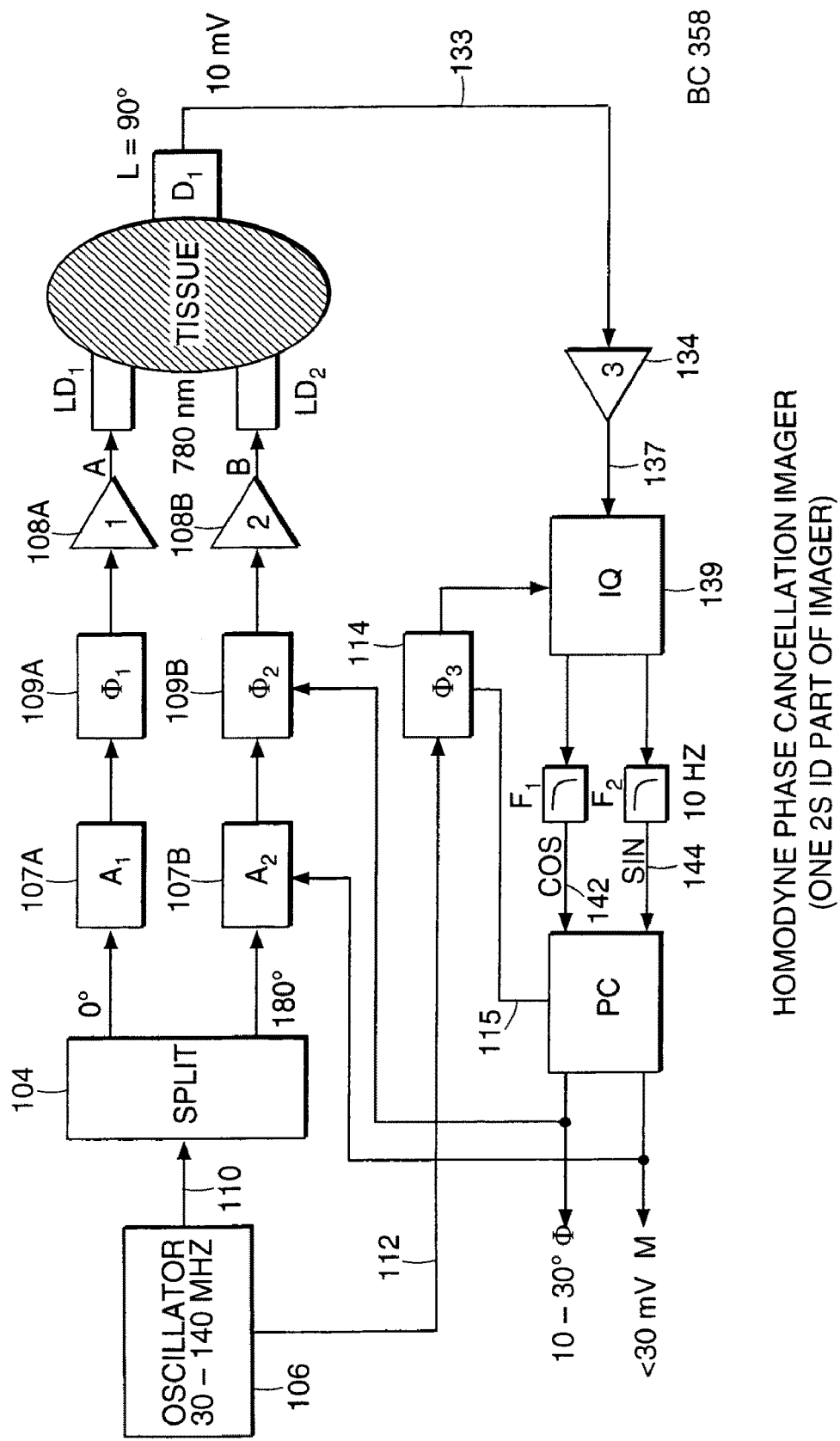

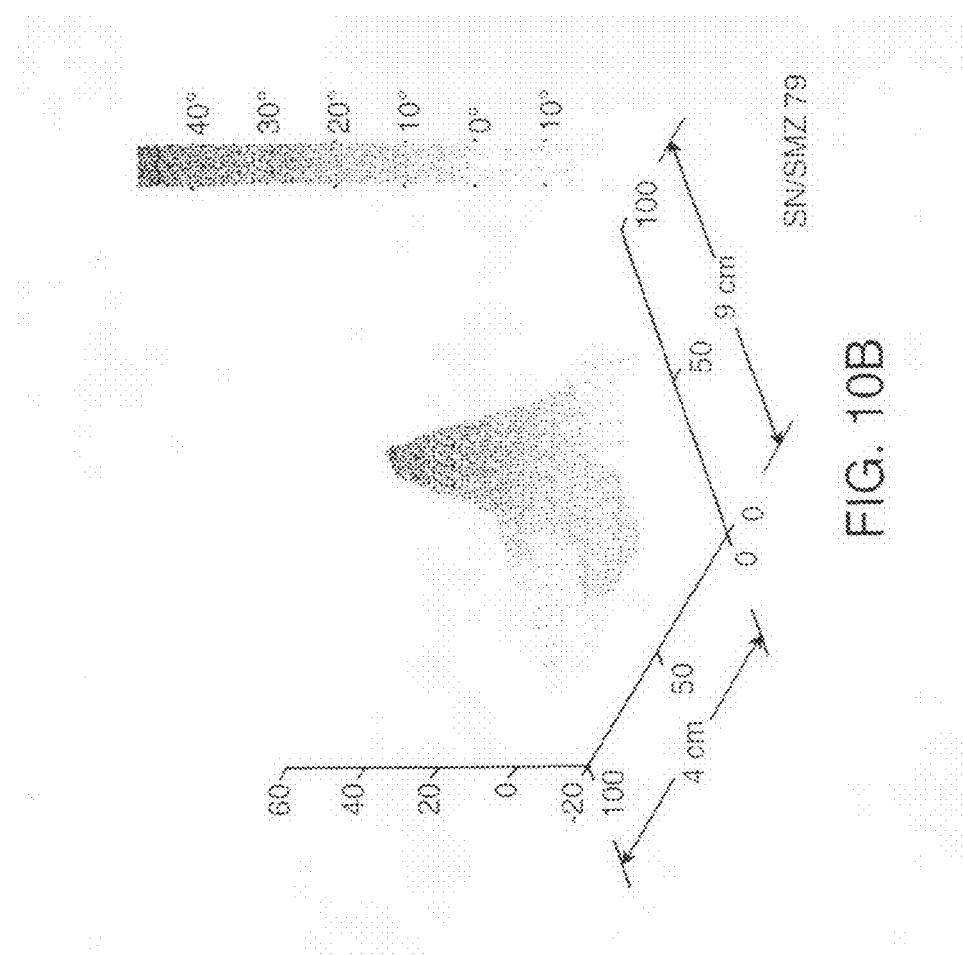
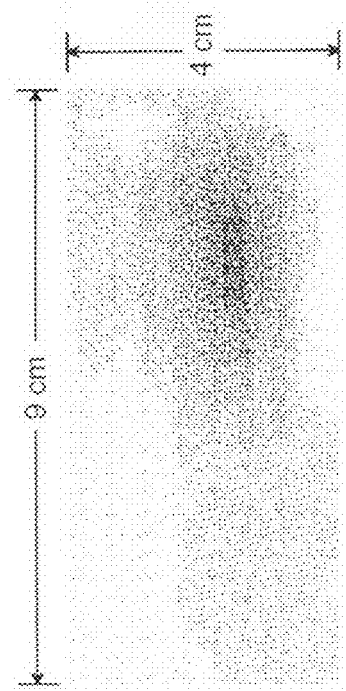
FIG. 10B
FIG. 10A

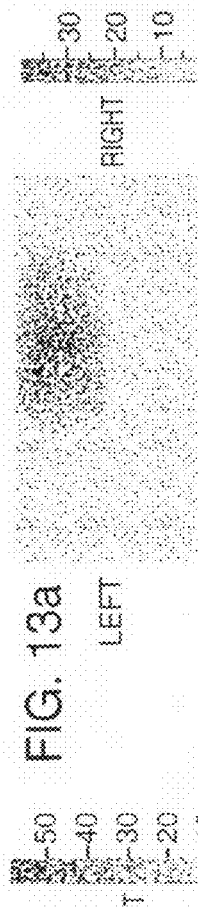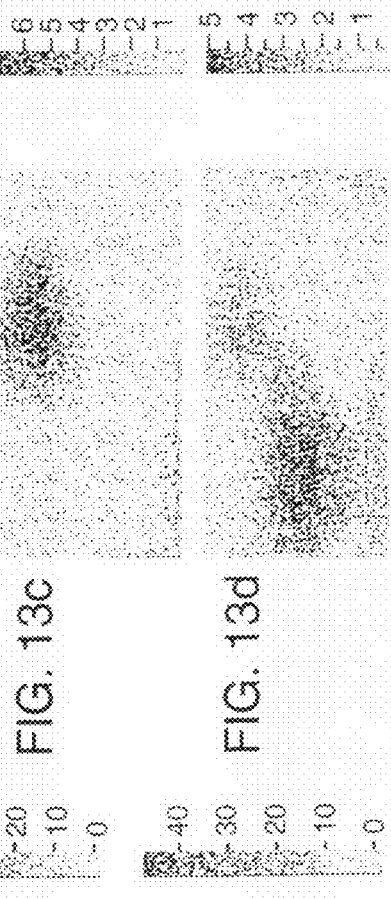
FIG. 12a
FIG. 12b
FIG. 12c
FIG. 13a
FIG. 13b
FIG. 13c
FIG. 13d

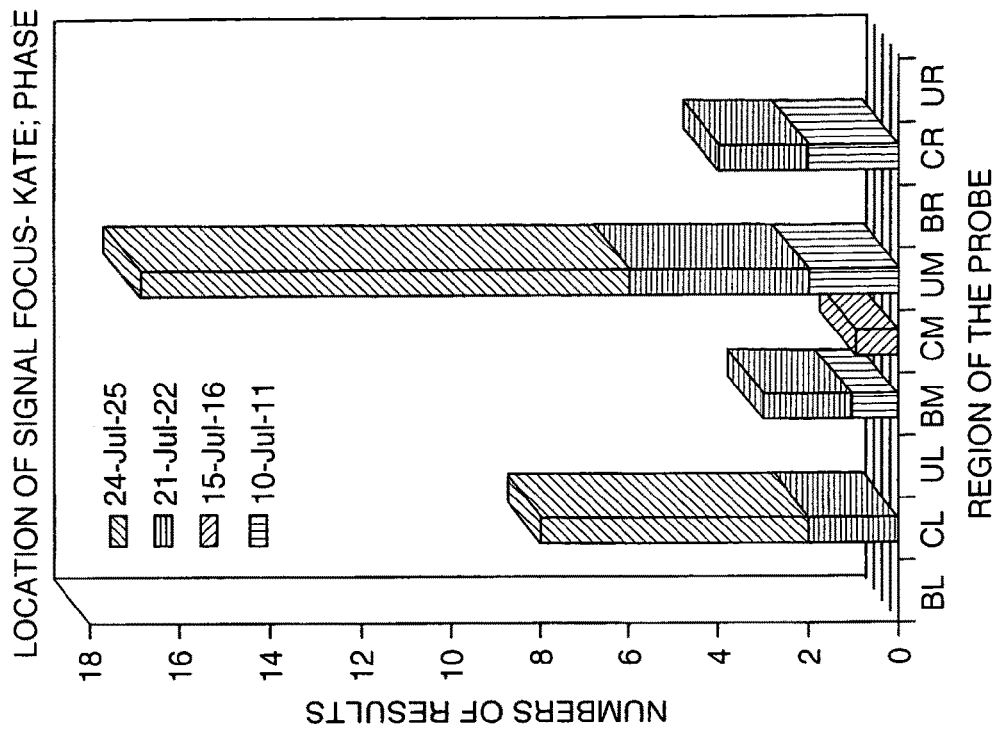
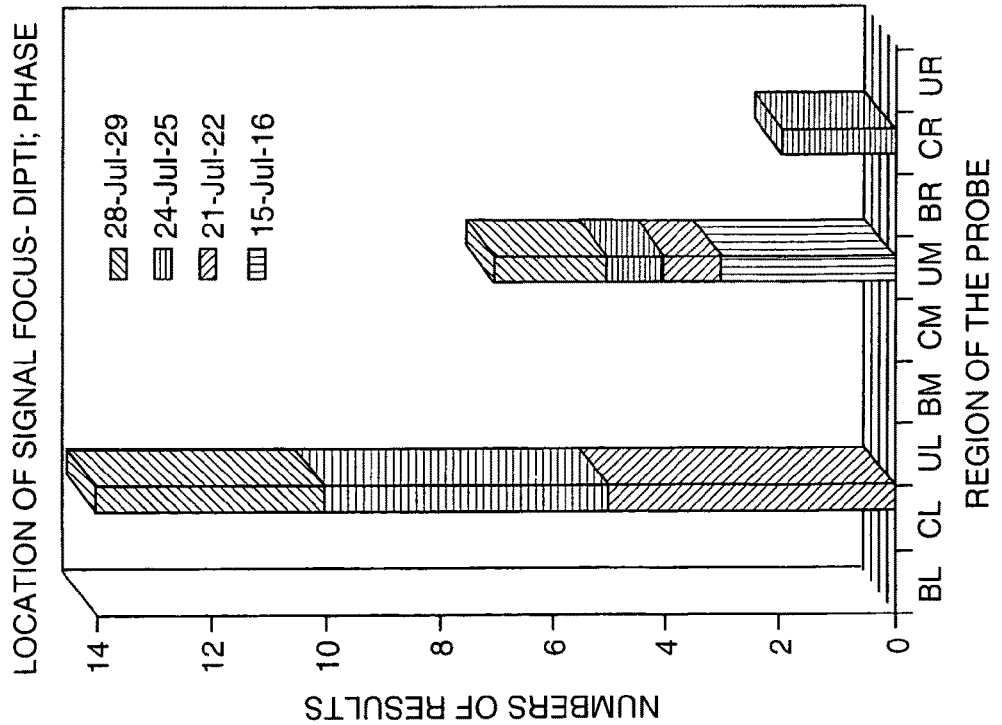
FIG. 14B
FIG. 14A

OPTICAL SYSTEM AND METHOD FOR IN-VIVO TRANSCRANIAL EXAMINATION OF BRAIN TISSUE OF A SUBJECT

This application is a continuation of U.S. application Ser. No. 09/622,112 filed Nov. 20, 2000, now abandoned, which is a §371 of PCT Application PCT/US99/03030, filed on Feb. 11, 1999, which claims benefit from U.S. Provisional Application Ser. No. 60/074,294 filed on Feb. 11, 1998, and from U.S. Provisional Application Ser. No. 60/098,018 filed on Aug. 26, 1998, all of which are incorporated by reference as if fully set forth herein.

THE FIELD OF THE INVENTION

The present invention relates to imaging and qualitative or quantitative characterization of biological tissue using visible or infra-red radiation, and more particularly to imaging and characterization of brain tissue.

BACKGROUND

Traditionally, X-rays or γ-rays has been used to examine and image biological tissue. This radiation propagates in the tissue on straight, ballistic tracks, i.e., scattering of the radiation is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer which reconstructs the X-ray absorption of the tissue at a multiplicity of points located in one cross-sectional plane.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing and thus, potentially causes fewer side effects. However, the visible or IR radiation is strongly scattered and absorbed in biological tissue, and the migration path cannot be approximated by a straight line, making inapplicable certain aspects of cross-sectional imaging techniques.

Computerized Tomography using NIR spectrometry has been used for in vivo imaging. This technique utilizes NIR radiation in an analogous way to the use of X-ray radiation in an X-ray CT. The X-ray source is replaced by several laser diodes emitting light in the NIR range. The NIR-CT uses a set of photodetectors that detect the light of the laser diodes transmitted through the imaged tissue. The detected data are manipulated by a computer similarly as the detected X-ray data would be in an X-ray CT. Different NIR-CT systems have recognized the scattering aspect of the non-ionizing radiation and have modified the X-ray CT algorithms accordingly.

The above-mentioned X-ray or γ-ray techniques have been used to detect a tissue tumor. Under the term "angiogenesis" I mean the generation of new blood vessels into a tissue or organ. Under normal physiological conditions humans or animals undergo angiogenesis only in very specific restricted situations. For example, angiogenesis is normally observed in wound healing, fetal and embryonal development and formation of the corpus luteum, endometrium and placenta.

Both controlled and uncontrolled angiogenesis are thought to proceed in a similar manner. Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases. The hypothesis that tumor growth is angiogenesis dependent was first proposed in 1971. (Folkman J., Tumor Angiogenesis: Therapeutic Implications., N. Engl. Jour. Med. 285: 1182-1186, 1971) In its simplest terms it states: "Once tumor 'take' has occurred, every increase in tumor cell population must be preceded by an increase in new capillaries converging on the tumor." Tumor 'take' is understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. This explanation was directly or indirectly observed and documented in numerous publications.

There is still a need for a non-invasive, relatively inexpensive technique that can detect, image and characterize a tumor alone or in conjunction with the above-mentioned techniques. Furthermore, there is still a need for a non-invasive, relatively inexpensive technique that can characterize brain tissue to detect a disease or functional abnormality.

SUMMARY

The present invention includes different novel apparatuses and methods for examination of biological tissue and specifically for transcranial optical examination or monitoring of the brain using visible or infra-red light. The optical examination technique can be used alone to detect and characterize a brain tissue anomaly or can be used in combination with X-ray techniques (including CT), magnetic resonance imaging (MRI or fMRI), or PET.

The novel techniques can employ different a single optical module placed on the head, or several optical modules placed on the right or left brain hemisphere of a patient that may be alert or even unconcious. If a suspicious structure in the head is detected, the technique can non-invasively characterize the structure (e.g., tissue mass, fluid volume) by taking optical data at different wavelengths and by generating one or several tissue specific characteristics related to the tissue metabolism (or hypermetabolism), biochemistry, pathophysiology (including angiogenesis) or another characteristic of a pathological tissue condition.

In one aspect, the optical examination technique employs an optical system for in vivo non-invasive examination of a volume of biological tissue of a subject. The optical examination system includes an optical module, a controller and a processor. The optical module includes an array of optical input ports and optical detection ports located in a selected geometrical pattern to provide a multiplicity of source-detector paths of photon migration inside the biological tissue. Each optical input port is constructed to introduce into the tissue volume visible or infrared light emitted from a light source. Each optical detection port is constructed to provide light from the tissue to a light detector. The controller is constructed and arranged to activate one or several light sources and light detectors so that the light detector detects light that has migrated over at least one of the source-detector migration paths. The processor receives signals corresponding to the detected light and creates a defined spatial image of the examined tissue.

The optical examination system may generate single wavelength or multiple wavelength images of the examined brain tissue, wherein the used wavelength is sensitive to absorption or scattering by a tissue constituent (e.g., an endogenous or exogenous pigment, tissue cells) or is sensitive to structural changes in the tissue. The optical images may display tissue absorption, tissue scattering or both. The optical imaging system may also generate blood volume, hemoglobin oxygenation images, and hemoglobin deoxygenation images (or images of any other tissue constituent) based on a single wavelength optical data or a multiple wavelength optical data. A processor may use different image processing and enhancing algorithms known in the art. The processor may correlate several images to detect a suspicious structure and then characterize the detected structure. The correlation includes determining congruency of the detected structures. The processor may employ different types of combined scoring, based on several optical images alone, or in combination with X-ray techniques, MRI or PET, to characterize a suspicious tissue mass.

The optical examination system may generate the above-described images of symmetrical tissue regions of the right brain and the left brain, symmetrical tissue regions of the brain lobes of the right brain and the left brain, or may generate images of both the entire right brain and the entire left brain. The optical examination system may also generate "model images" of by irradiating a model constructed to have scattering and absorptive propertied of a selected tissue region. The optical examination system may also separately calibrate its sources and detectors on a model. To identify and characterize a suspicious tissue mass, the processor may employ the different types of combined scoring by correlating the different images mentioned above.

The optical imaging system may collect single wavelength or multiple wavelength data of a brain tissue model for calibration, or for detection of background data. In the calibration procedure, the optical module is placed on the model and the imaging system can collect a limited number of optical data or can collect optical data using the same sequences used during the tissue examination. The system may either collect and store the model data for a subsequent digital processing, or may adjust the source or detector gains to detect optical data according to a selected pattern. The imaging system may use different head models having the same scattering coefficient and the same absorption coefficient as the normal brain tissue and the same scattering coefficient and the same absorption coefficient as the normal skull. The model tissue may have the scattering and absorption coefficient of infected cerebral tissue, tissue with cerebral vasculitis, Parkinson's disease, Alzheimer's disease, or multiple sclerosis. Furthermore, the models may have different sizes and shapes.

To characterize the examined tissue, the imaging system can correlate several images of blood volume, hemoglobin oxygenation, hemoglobin deoxygenation, or images sensitive to an optical contrast agent. The imaging system can correlate images of the same tissue region taken at different times. The correlation of the images identifies pathological tissue regions, such as tumors undergoing angiogenetic growth wherein the tumor area exhibits an increased blood volume and decreased hemoglobin oxygenation. Furthermore, the correlation of the images can be used to monitor inhibition of angiogenesis during or after drug treatment.

The described optical systems can also provide amplitude or phase cancellation patterns that demonstrated for single or multiple source-detector pairs remarkable sensitivity and were used to detect small objects. Using back-projection algorithms or other known imaging algorithms, the described optical systems can image sensorimotor activation of adult and pre- and full-term neonate human brain function and achieve two dimensional resolutions of less than 1 cm. In addition, the optical system records rapidly and accurately sensorimotor responses in pre- and full-term infants. The present systems and methods can be used in evaluation of cerebral dysfunctions or pathologies of adults, children, infants or neonates.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue. Each optical input port is constructed to introduce visible or infrared light emitted from a light source. Each optical detection port is constructed to receive photons of light that have migrated in the examined tissue region from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets, a first of the data sets representing blood volume in the examined tissue region and a second of the data sets representing blood oxygenation in the examined tissue region. The processor is arranged to correlate the first and second data sets to detect abnormal tissue in the examined tissue region.

Preferably, the second data set includes hemoglobin deoxygenation values. The processor may be arranged to form a third data set being collected by irradiating a reference tissue region.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue. Each optical input port is constructed to introduce visible or infrared light emitted from a light source. Each optical detection port is constructed to receive photons of light that have migrated in the tissue from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets, a first of the data sets being collected by irradiating an examined tissue region of interest and a second of the data sets being collected by irradiating a reference tissue region having similar light scattering and absorptive properties as the examined tissue region. The processor is arranged to correlate the first and second data sets to detect abnormal tissue in the examined tissue region.

According to another aspect, the optical examination technique employs an optical system for in vivo, non-invasive examination of biological tissue of a subject. The optical system includes an optical module, a controller, and a processor. The optical module includes an array of optical input ports and detection ports located in a selected geometrical pattern to provide a multiplicity of photon migration paths inside an examined region of the biological tissue or a model representing biological tissue. Each optical input port is constructed to introduce visible or infrared light emitted from a light source. Each the optical detection port is constructed to receive photons of light that have migrated in the tissue or the model from at least one of the input ports and provide the received light to a light detector. The controller is constructed and arranged to control operation of the light source and the light detector to detect light that has migrated over at least one of the photon migration paths. The processor is connected to receive signals from the detector and arranged to form at least two data sets of two tissue regions, a first of the data sets being collected by irradiating an examined tissue region and a second of the data sets being collected by irradiating a region of a tissue model having selected light scattering and absorptive properties. The processor is arranged to correlate the first and second data sets to detect abnormal tissue in the examined tissue region.

Preferred embodiments of these aspects of the inventions have one or more of the following features.

The processor may be arranged to correlate the first and second data sets by determining congruence between data of the two data sets.

The processor may be programmed to order the first and second data sets as two-dimensional images and to determine the congruence using the two-dimensional images. The processor may be programmed to order the first and second data sets as two-dimensional images and to determine the congruence using the following formula:

$$1 - \left(\frac{\text{maximum overlap residual}}{\text{maximum selected tissue signal}}\right) \times 100$$

The processor may be further arranged to determine a location of the abnormal tissue within the examined tissue region.

The processor may be adapted to produce from the data set an image data set by implementing an optical tomography algorithm. The optical tomography algorithm may use factors related to determined probability distribution of photons attributable to the scattering character of the tissue being imaged.

The controller may be arranged to activate the source and the detector to obtain a first selected distance between the input and detection ports, and the processor may be arranged to form the data set for the first distance. The processor may produce an image data set from the data set formed for the first distance. The controller may further be arranged to activate the source and the detector to obtain a second selected distance between the input and detection ports and is arranged to form another data set for the second distance.

The optical system may further include a display device constructed to receive the image data set from the processor and to display an image.

The optical system may further include a first oscillator and a phase detector. The first oscillator is constructed to generate a first carrier waveform at a first frequency on the order of $10^8$ Hz, the first frequency having a time characteristic compatible with the time delay of photon migration from the input port to the detection port. The light source is coupled to the first oscillator and constructed to generate the light modulated by the first carrier waveform. The phase detector is constructed to determine change in waveform of the detected light relative to the waveform of the introduced light and measure therefrom the phase shift of the detected light at the wavelength, wherein the phase-shifted light is indicative of scattering or absorptive properties of the examined tissue region. The processor is arranged to form the data set based on the measured phase shift. This optical system may further include a second oscillator constructed to generate a second waveform at a second frequency. The detector is then arranged to receive a reference waveform at a reference frequency offset by a frequency on the order of $10^3$ Hz from the first frequency and to produce a signal, at the offset frequency, corresponding to the detected radiation. The phase detector is adapted to compare, at the offset frequency, the detected radiation with the introduced radiation and to determine therefrom the phase shift.

The optical system may further include an oscillator, a phase splitter, and first and second double balanced mixers. The oscillator is constructed to generate a first carrier waveform of a selected frequency compatible with time delay of photon migration from the input port to the detection port The light source is connected to receive from the oscillator the carrier waveform and is constructed to generate optical radiation modulated at the frequency. The phase splitter is connected to receive the carrier waveform from the oscillator and produce first and second reference phase signals of predefined substantially different phases. The first and second double balanced mixers are connected to receive from the phase splitter the first and second reference phase signals, respectively, and are connected to receive from the detector the detector signal and to produce therefrom a in-phase output signal and a quadrature output signal, respectively. The processor being connected to the double balanced mixers and arranged to receive the in-phase output signal and the quadrature output signal and form therefrom the data set.

The processor may be arranged to calculate a phase shift ($\Theta_\lambda$) between the light introduced at the input port and the light detected at the detection port prior to forming the data set.

The processor may arranged to calculate an average migration pathlength of photons scattered in the examined tissue between the optical input port and the optical detection port prior to forming the data set.

The processor may further employ the pathlength in quantifying hemoglobin saturation (Y) of the examined tissue.

The processor may be arranged to calculate a signal amplitude ($A_\lambda$) determined as a square root of a sum of squares of the in-phase output signal and the quadrature output signal prior to forming the data set.

The optical system may further include a narrow band detector connected to receive from the optical detector the detector signal and to produce a DC output signal therefrom. The processor then further determines a modulation index ($M_\lambda$) as a ratio of values of the signal amplitude and the signal amplitude plus the DC output signal.

The optical system may further include at least one oscillator connected to at least one light source. The oscillator is constructed to generate a carrier waveform of a selected frequency. The light source generate slight of a visible or infrared wavelength being intensity modulated at the frequency to achieve a known light pattern. The controller is constructed to control the emitted light intensity or phase relationship of patterns simultaneously introduced from multiple input ports, wherein the introduced patterns form resulting radiation that possesses a substantial gradient of photon density in at least one direction. This resulting radiation is scattered and absorbed over the migration paths. The detector is constructed and arranged to detect over time the resulting radiation that has migrated in the tissue to the detection port. The processor is further arranged to process signals of the detected resulting radiation in relation to the introduced radiation to create the data sets indicative of influence of the examined tissue upon the substantial gradient of photon density of the resulting radiation.

The optical system may further include a phase detector constructed to detect the phase of the detected radiation and provide the phase to the processor.

The optical system may further include an amplitude detector constructed to detect the amplitude of the detected radiation and provide the amplitude to the processor.

The phase relationship of light patterns introduced from two input ports may be 180 degrees.

The optical system may be constructed as described in U.S. Pat. No. 5,119,815 or 5,386,827. This system includes a light source constructed to generate pulses of radiation of the wavelength, the pulses having a known pulse wave form of a duration on the order of a nanosecond or less. An optical detector is constructed to detect over time photons of modified pulses that have migrated in the tissue from the input ports. This system also includes an analyzer connected to the detector and adapted to determine a change in the pulse waveform shape of the detected pulses relative to the introduced pulses, at the employed wavelength. The processor then creates the data set based on the determined pulse waveform change. The processor may also be constructed and arranged to calculate the effective pathlength of photons of the wavelength migrating between the input and detection ports in conjunction with creating the data set. The processor may also be constructed and arranged to calculate the scattering coefficient at the wavelength in conjunction with creating the image data set The processor may also be constructed and arranged to calculate the absorption coefficient at the wavelength in conjunction with creating the data set.

The optical system may use the light source that produces relatively long light pulses and the processor that forms the data set by subtracting amplitude of two the pulses emitted from two input ports located symmetrically relative to one detection port.

The optical system may be constructed to introduce and detect photons at two wavelengths selected to be sensitive to a tissue constituent. The tissue constituent may be an endogenous pigment or an exogenous pigment. The endogenous pigment may be hemoglobin. The exogenous pigment may be a selected contrast agent.

According to another aspect, an optical system for in vivo, non-invasive imaging of tissue change includes an optical module including an array of input ports and detection ports located in a selected geometrical pattern to provide a multiplicity of arrayed single source, single detector pairs engaged directly with the subject. The optical system also includes a spectrophotometer with a light source means constructed to introduce electromagnetic radiation of visible or infra-red wavelength into the examined tissue successively at the input ports, the wavelength being sensitive to a constituent of the imaged tissue, and detector means constructed to detect, at the detection ports, radiation of the selected wavelength that has migrated in the tissue from respective input ports. The spectrophotometer also includes a processor connected to receive signals of the detected radiation from the detector means and constructed to create a defined spatial image of the tissue by effectively producing from signals from the multiplicity of arrayed single source, single detector pairs, a succession of data sets representing, from a selected view, a succession of spatial images of the tissue, and an image data set related to differences between data of the successive data sets.

According to another aspect, an optical system is provided for in vivo, non-invasive functional neuroimaging of brain tissue. The optical system include a stimulator constructed to stimulate a selected functional activity of neural tissue of interest, an optical module including an array of input ports and detection ports located in a selected geometrical pattern to provide a multiplicity of arrayed single source, single detector pairs engaged directly with the subject, a spectrophotometer including light source means constructed to introduce electromagnetic radiation of visible or infra-red wavelength into the examined neural tissue successively at the input ports, the wavelength being sensitive to a tissue constituent associated with a physiological response of the imaged functional activity, detector means constructed to detect, at the detection ports, radiation of the selected wavelength that has migrated in the stimulated neural tissue from respective input ports, and a processor receiving signals of the detected radiation from the detector means, and constructed and arranged to create a defined spatial image of the functional activity of neural tissue by effectively producing from the signals from the multiplicity of arrayed single source, single detector pairs, a first data set representing, from a selected view, a spatial image of the neural tissue at rest, a second data set representing, from the same selected view, a spatial image of the neural tissue during stimulation, and a functional image data set that is related to the differences between the first and second data sets, over the sets.

According to another important aspect, an instrument is provided for functional imaging of brain activity of a subject comprising an imager constructed and arranged to image oxyhemoglobin, deoxyhemoglobin or blood volume. The imager includes an array of sources of near infrared or visible photons, and array of detectors positioned to receive photons from the sources following migration of photons from the sources through the tissue. The imager enables numerous readings of migrated photons to be taken systematically for different source-detector positions relative to the tissue, and a processor employing data sets taken during rest and during stimulation, with an imaging algorithm that is based on respectively different probabilities for a given source-detector position, for photons from the source passing through different regions of the volume of the scattering tissue that are located at different positions distributed laterally from a straight reference line between source and detector.

Preferred embodiments of these aspects of the inventions have one or more of the following features.

The optical module is constructed to maintain a selected distance between the input and detection ports for the respective source-detector pairs during the production of the first and second data sets, the distance being selected according to the tissue depth desired to be imaged.

To characterize the examined tissue, the imaging system can correlate several images of blood volume, hemoglobin oxygenation, hemoglobin deoxygenation, or images sensitive to an optical contrast agent, prior and after stimulation. The imaging system can also correlate the images taken over time without stimulation. The correlation of the images identifies pathological tissue regions or dysfunctional tissue regions of the brain.

The optical module or an associated set of the modules is constructed to detect light that has migrated in the tissue at different depths to produce 3D data sets from which an image data set may be produced.

The processor is adapted to produce the image data set by implementing an optical tomography algorithm.

The optical tomography algorithm preferably employs factors related to determined probability distribution of photons attributable to the scattering character of the tissue being imaged.

The optical system is constructed to form the image data set from a part of the head. In particular embodiments the optical system is constructed to form the functional image data set from below the surface region of the cortex.

The stimulator is constructed to stimulate the visual cortex, the cognitive cortex, the sensory motor cortex, or spinal tissue. In various embodiments, the stimulator is constructed to deliver electrical signals to selected tissue, apply an electrical field to selected tissue, or deliver magnetic signals to selected tissue.

In various embodiments the image set is related to at least one of the group consisting of blood volume, hemoglobin oxygenation or deoxygenation, photon absorption coefficient, photon scattering coefficient, refractive index, change in magnetic field, change in electric field, production of or change of a specific tissue constituent, and production of or change in the concentration of a tissue constituent The tissue constituent may be an endogenous pigment, for example hemoglobin, or an exogenous pigment, for example a selected optical contrast agent.

The source means, the detector means, the source to detector distance, and the rate of excitation and detection are selected to enable an image data set to be obtained within a short time, i.e., within minutes, preferably within a minute or less.

Each source is laterally displaced from its detector or detectors (or each detector is laterally displaced from its source or sources) on the surface of a subject at a side by side spacing between about 1 cm and 10 cm (preferably 1.5 cm and 7 cm) to establish a banana-shaped probability gradient of migrating photons in the tissue that extends from source to detector.

The invention also features methods of producing an image from a volume of light-scattering tissue of a living subject comprising, providing and employing on the subject an imaging instrument according to any of the foregoing aspects. In certain preferred embodiments of the methods an optical contrast agent or a drug is introduced to the blood stream of the subject, and the instrument is employed to produce an image data set for the tissue while the contrast agent or drug is present in blood circulating in the tissue of the subject or is present in localized tissue.

Other advantages and features of the invention will be apparent from the following description of the preferred embodiment and from the claims.

BRIEF DESCRIPTION OF THE DRAWINGS

FIGS. 1 and 1A show an optical module located on the forehead of a subject.

FIGS. 2, 2A and 2B show another embodiment of the optical module located on the forehead of the subject.

FIG. 3B is a timing diagram used by the imaging system of FIGS. 3 and 3A.

FIGS. 4 and 4A show diagrammatically another embodiment of the phase cancellation imaging system employing the optical module of FIG. 1A or FIG. 2A.

FIGS. 10A and 10B show an experimental optical image obtained by the imaging system of FIG. 3 with contralateral, parietal finger touching as a stimulation.

FIGS. 12A through 13D show prefrontal cortex optical images detected by the optical imaging system of FIG. 3 during a cognitive activity of subjects.

FIGS. 14A and 14B are histograms of the positions on the forehead for two subjects.

DESCRIPTION OF THE PREFERRED EMBODIMENTS

Figure 3:
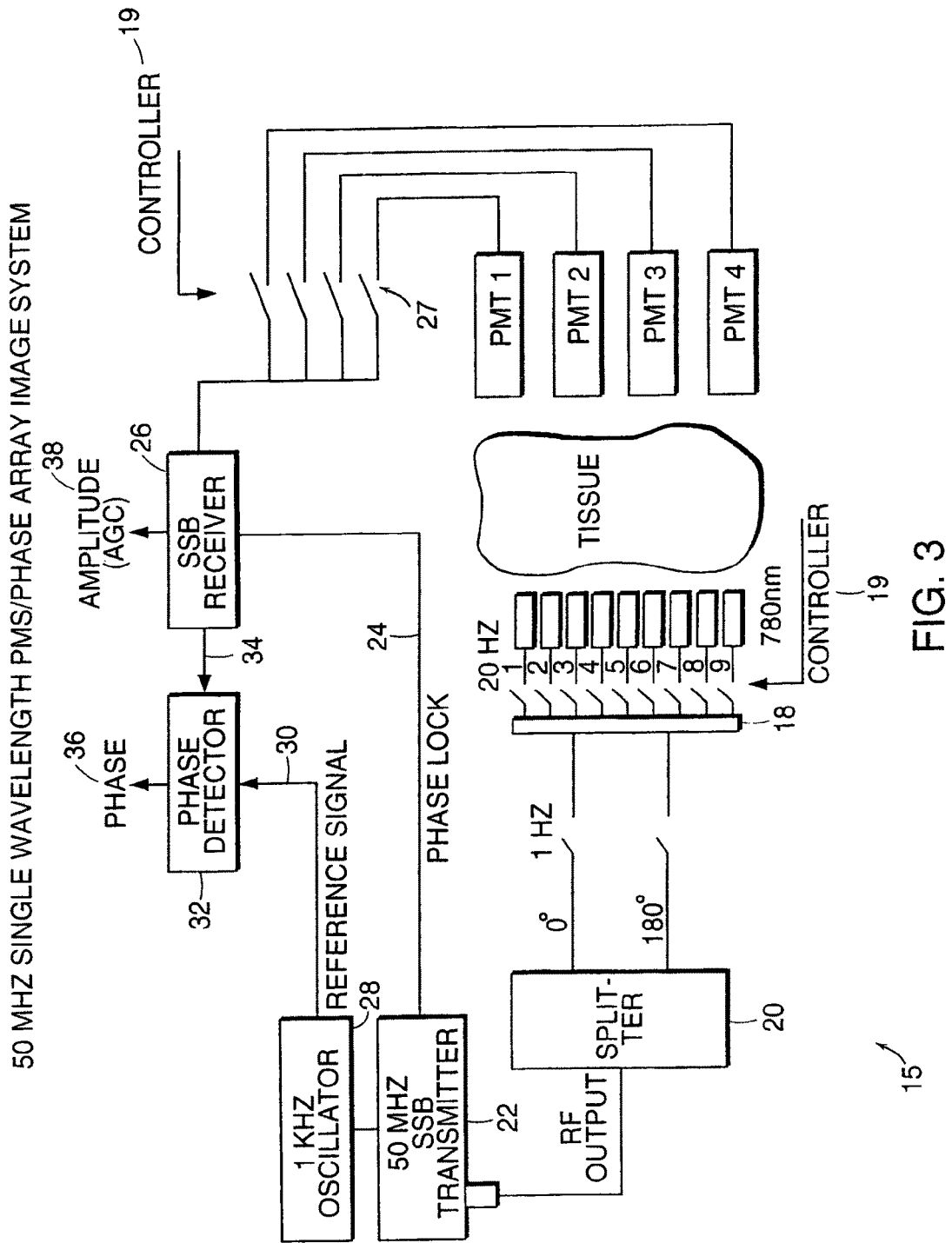
FIGS. 3 and 3A show diagrammatically respective single wavelength and dual wavelength phase cancellation imaging systems that employ the optical module of FIG. 1A or FIG. 2A.

Referring to FIGS. 1, 1A, 2 and 2A the brain tissue of a subject 8 is examined using an imaging system connected to an optical module 12 or 14. Optical modules 12 and 14 include a multiplicity of light sources (e.g., laser diodes, LEDs, flashlight bulbs) providing light in the visible to infrared range; and light detectors (e.g., photo multiplier tubes, Si diode detector, PIN, avalanche or other diode detectors), which may also include interference filters. Fig. 2B shows two optical modules 14. The light sources and the light detectors are arranged to form selected geometrical patterns that provide a multiplicity of source-detector paths of photon migration inside the brain tissue. An optical examination system provides an in vivo optical data of the examined tissue, and the data may be processed to create an image. The image can show a location and size of an abnormal structure in the tissue, such as a tumor or bleeding. Furthermore, the optical data can provide a qualitative and quantitative measure (e.g., metabolism, metabolic biochemistry, pathophysiology) of an abnormal tissue structure. (Alternatively, an optical module includes a multiplicity of optical fibers connected to one or several light sources, and a multiplicity of optical detection fibers connected to one or several light detectors as described in the PCT applications PCT/US96/00235 and PCT/US96/11630 (filed Jan. 2, 1996 and Jul. 12, 1996).)

In one embodiment, optical module 12 includes nine laser diodes $S_1, S_2, \ldots, S_9$ and four photo multiplier tubes (PMTs) $D_1, D_2, D_3, D_4$. The laser diodes and PMTs are embedded in a pliable rubber-like material positioned in contact with the scalp. There may be a Saran® wrap or similar material located between the laser diodes and the skin, and between the PMTs and the skin. Similarly, optical module 14 includes four laser diodes $S_1$, $S_2$, $S_3$, $S_4$ and 27 silicon diode detectors $D_1$, $D_2$, ..., $D_{27}$ embedded in a pliable rubber-like material. The optical systems shown in FIGS. 3 through 7 may be interfaced with optical module 12 or 14 for imaging of the brain tissue. Optical modules 12 and 14 have pairs of optical input ports symmetrically located (or equidistantly located) relative to an optical detection port, or have pairs of optical detection ports symmetrically located relative to an optical input port In general, however, the ports do not have to be positioned symmetrically. The optical systems can vary the source or detector gain to account for any positional asymmetry or can introduce a selected asymmetry by adjusting the source or detector gain.

Furthermore, the systems shown in FIGS. 3 through 7, may be interfaced with two identical optical modules (12 or 14) located on symmetrical brain tissue, such as the right brain hemisphere and the left brain hemisphere for lateralization, that is, comparative tissue examination the right brain hemisphere and the left brain hemisphere. The comparative examination may be performed on the individual brain lobes, such as the right temporal lobe and the left temporal lobe, the right occipital lobe and the left occipital lobe, or the right parietal lobe and the left parietal lobe of the brain. Alternatively, the comparative examination may be performed on symmetric tissue of the same lobe, such as the frontal lobe. For calibration, the optical module may also be placed on one or several models of the head having the same scattering coefficient and the same absorption coefficient as the normal brain tissue including the skull.

Referring to FIGS. 1A and 3, a phased array imaging system 15 is connected to optical module 12 with nine laser diodes $S_1$, $S_2$, ..., $S_9$ and four PMTs $D_1$, $D_2$, $D_3$, $D_4$ (e.g., Hamamatsu R928, Hamamatsu R1645u, TO8) powered by a high voltage supply (not shown). Four laser diodes surround each PMT forming an equidistant arrangement (for example, different optical modules may use distances of 3.5, 7 and 10.5 cm). A switch 18 connects laser diodes $S_1$, $S_2$, ..., $S_9$ to a phase splitter 20, which provides to the diodes an RF modulation signal having both a 0 degree phase and a 180 degree phase. Imaging system 15 also includes a 50 MHZ single side band transmitter 22 connected by a phase lock loop 24 to a 50 MHZ single side band receiver 26. Single side band (SSB) transmitter 22 is connected to a 1 kHz oscillator 28, which provides a reference signal 30 to a phase detector 32. SSB receiver 26 is connected to a switch 27, which connects one of the four PMTs (0.5 µV sensitivity) depending on control signals from a controller 19. The SSB transmitter-receiver pair can operate in the frequency region of 10-1000 MHZ (preferably 50-450 MHZ). The SSB receiver detects signal levels on the order of microvolts in a 2 KHz bandwidth. The phase noise of this apparatus is less than about 0.1°. However, this narrow bandwidth limits the spread of switching of various light sources to approximately 1.0 msec, and thus the sequencing time for an entire image of 16 source detector combinations can be ~1 sec. The system uses a 1 sec averaging time.

Controller 19, connected to a personal computer (not shown), sequences laser diodes $S_1$, $S_2$, ..., $S_9$ So that two diodes receive 0° phase and 180° phase signals from splitter 20, every 0.1 sec. At the same time, controller 19 connects a symmetrically located PMT to SSB receiver 26. As shown in a timing diagram 40 (FIG. 3B), phased array imaging system 15 triggers two sources so that they emit modulated light of a 0° phase and a 180° phase for about 100 msec, and at the same time triggers a symmetrically located PMT. For example, when laser diodes 1 ($S_1$) and 2 ($S_2$) emit light of a 0° and 180° phase, respectively, and detector 1 ($D_1$) detects light that has migrated in the examined tissue. SSB receiver 26, which is phase locked with SSB transmitter 22, receives signal from detector 1 and provides output signal 34 to phase detector 32. Phase detector 32 measures the phase (36) of the detected light, and SSB receiver 26 provides the amplitude (38) of the detected light. This phase detection circuit was described in U.S. Pat. No. 4,972,331, which is incorporated by reference.

In the next cycle, controller 19 directs switch 18 to connect laser diodes 2 ($S_2$) and 3 ($S_3$), which emit modulated light of a 0° phase and a 180° phase, respectively, and detector 2 ($D_2$) detects light that has migrated in the examined tissue. Controller 19 also directs switch 27 to connect detector 2 to SSB receiver 26, which receives detection signal corresponding to the photons that have migrated from laser diodes 2 and 3 to detector 2. Again, phase detector 32 measures the phase (36) of the detected light, and SSB receiver 26 provides the amplitude (38) of the detected light. The duration of each pair of light flashes is 100 msec. The complete set of data for all source detector combinations is collected every 30 sec. A computer (not shown) stores the phase values and the amplitude values measured for the different combinations shown in timing diagram 40 and employs these values to create images of the examined tissue, as is described below. The computer uses the ADA2210 board for data acquisition.

Before or after the above-described measurement, phased array imaging system 15 may be calibrated on a model of the skull and brain tissue. In the calibration procedure, the optical module is placed on the model and the imaging system collects the phase data and the amplitude data using the sequences shown in the timing diagram 40. The imaging system may use different models having the same scattering coefficient and the same absorption coefficient as the normal brain tissue, a brain that suffered trauma manifested as cerebral edema, cerebral contusion, intracranial hemorrhage. The model tissue may have scattering and absorption coefficient of infected cerebral tissue, tissue with cerebral vasculitis, Parkinson's disease, Alzheimer's disease or multiple sclerosis. Furthermore, the models may have different sizes and shapes.

Phased array imaging system 15 generates a "model" image for each wavelength employed. The model image may later be subtracted from the brain images to calibrate the system and also account for the boundary conditions of the light migrating in the tissue. Alternatively, phased array imaging system 15 is calibrated prior to taking measurement data and the gain on the light sources or the detectors is adjusted to obtain selected values.

Figure 3A:
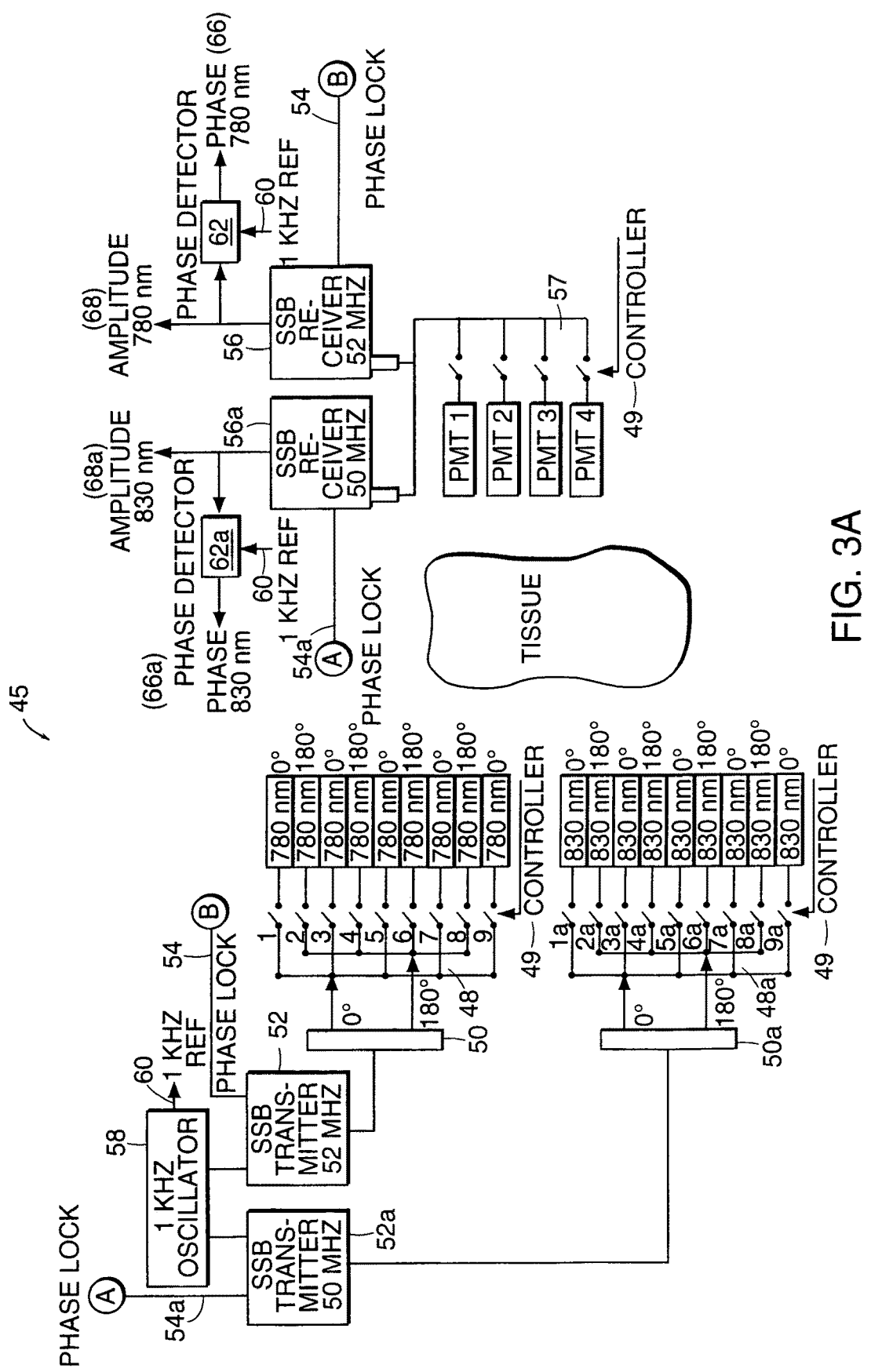

Referring to FIGS. 1A and 3A, a dual wavelength phased array imaging system 45 is connected to optical module 12 with nine 780 nm laser diodes $S_1$, $S_2$, ..., $S_9$, nine 830 nm laser diodes $S_{1a}$, $S_{2a}$, ..., $S_{9a}$, and the four PMTs $D_1$, $D_2$, $D_3$, and $D_4$ powered by a high voltage supply (not shown). Pairs of laser diodes $S_1$ and $S_{1a}$, $S_2$ and $S_{2a}$, ..., $S_9$ and $S_{9a}$ are located next to each other and arranged to introduce modulated light at almost the same tissue locations. A switch 48 connects laser diodes $S_1$, $S_2$, ..., $S_9$ to a phase splitter 50, which provides to the laser diodes an RF modulation signal having both a 0 degree phase and a 180 degree phase. Similarly, a switch 48a connects laser diodes $S_{1a}$, $S_{2a}$, ..., $S_{9a}$ to a phase splitter 50a, which provides to the laser diodes an RF modulation signal having both a 0 degree phase and a 180 degree phase. A 52 MHZ SSB transmitter 52 is connected by a phase lock loop 54 to a 52 MHZ SSB receiver 56, and a 50 MHZ SSB transmitter 52a is connected by a phase lock loop 54a to a 50 MHZ SSB receiver 56a. Both SSB transmitters 52 and 52a are connected to a 1 kHz oscillator 58, which provides a reference signal 60 to phase detectors 62 and 62a. SSB receivers 56 and 56a are connected one of the four PMTs by a switch 57 depending on control signals from controller 49. Controller 49, connected to a personal computer, sequences the laser diodes so that two pairs of the laser diodes receive 0° phase and 180° phase signals from splitters 50 and 50a, and at the same time controller 49 connects a symmetrically located detector to SSB receivers 56 and 56a.

As shown in timing diagram 40 (FIG. 3B), phased array imaging system 45 triggers for each wavelength two sources that emit simultaneously modulated light of a 0° phase and a 180° phase for about 100 msec and, at the same time, controller 49 connects the symmetrically located PMT. For example, switch 48 connects SSB transmitter 52 to 780 nm laser diode 4 ($S_4$) to emit 52 MHZ modulated light of a 180° phase and connects 780 nm laser diode 5 ($S_5$) to emit 52 MHZ modulated light of a 0° phase. At the same time, switch 48a connects SSB transmitter 52a to 830 nm laser diode 4a ($S_{4a}$) to emit 50 MHZ modulated light of a 180° phase and connects 830 nm laser diode 5a ($S_{5a}$) to emit 52 M modulated light of a 0° phase. Simultaneously, switch 57 connects detector 1 ($D_1$) to SSB receivers 56 and 56a to receive the detection signal corresponding to photons of both wavelengths that have migrated in the examined tissue.

Phase detector 62 provides the phase (66) of the detected 780 nm light, and phase detector 62a provides the phase (66a) of the detected 830 nm light for the selected geometry. Similarly, SSB receiver 56 measures the amplitude (68) of the detected 780 nm light and SSB receiver 56a measures the amplitude (68a) of the detected 830 nm light. This operation is repeated for all combinations of sources and detectors shown in timing diagram 40. A computer (not shown) stores the phase values and the amplitude values (at each wavelength) measured for the different combinations shown in tiling diagram 40. The computer then uses the measured values to create images using algorithms included the enclosed source code. Initially, the system takes quick pictures to find the area of interest so that the optical module can be moved around to find an optimal geometry. Once found, the 780 nm and 830 nm data (i.e., both the phase and amplitude data) is acquired and saved on a disk.

Several phased array systems were described in the PCT application PCT/US 93/05868 (published as WO 93/2514 on Dec. 23, 1993), which is incorporated by reference. This PCT publication also describes the basic principles of phase and amplitude cancellation. The phased array imaging system uses a detector for detecting light emitted from equidistant sources located symmetrically with respect to the detector (or one source and several equidistant detectors located symmetrically). If two sources $S_1$ and $S_2$ emit modulated light having equal amplitude and a 0° phase and a 180° phase, detector $D_1$ located in the middle detects a null in the amplitude signal and detects a crossover between the 0° and 180° phase, i.e., a 90° phase, for substantially homogeneous tissue. That is, the detector is located on the null plane. In heterogeneous tissue, the null plane is displaced from the geometric midline. Nevertheless, the null establishes an extremely sensitive measure to perturbation by an absorber or scatterer. Furthermore, at the null condition, the system is relatively insensitive to amplitude fluctuations common to both light sources, and insensitive to inhomogeneities that affect a large tissue. The system has a high sensitivity to scattering provided that the scattering contrast is the same as the absorbing contrast. The system can readily observe shifts of 50 to 60° of phase under altered blood volume or blood oxygenation conditions, where the phase noise is less than a 0.10 (s/n>400) for a 1 Hz bandwidth. The amplitude signal is little less useful in imaging since the position indication is somewhat ambiguous, i.e., an increase of signal is-observed regardless of the displacement of the absorbing object with respect to the null plane, although this is remedied by further encoding of the sources.

As described in the PCT application PCT/US 93/05868, the light sources excite a photon diffusion wave, due to cancellation effects, which has a relatively long wavelength (~10 cm), determined by the scattering ($\mu_s'$=10 cm$^{-1}$) and absorption ($\mu_a$=0.04 cm$^{-1}$) properties of the tissue. The photon diffusion wavelength of about 10 cm provides imaging in the "near field." The imaging system may use light sources of one or several optical wavelengths in the visible to infrared range, depending on the characteristic to be imaged (i.e., blood volume, blood oxygenation, a distribution of a contrast agent in the tissue, an absorbing constituent of the tissue, a fluorescing constituent of the tissue, or other). The phase signal at zero crossing detection is essentially a square wave "overloaded" signal. It is moderately insensitive to the changes of signal amplitude that may occur in imaging from proximal to distal source-detector pairs and is also moderately insensitive to ambient light.

Figure 4:
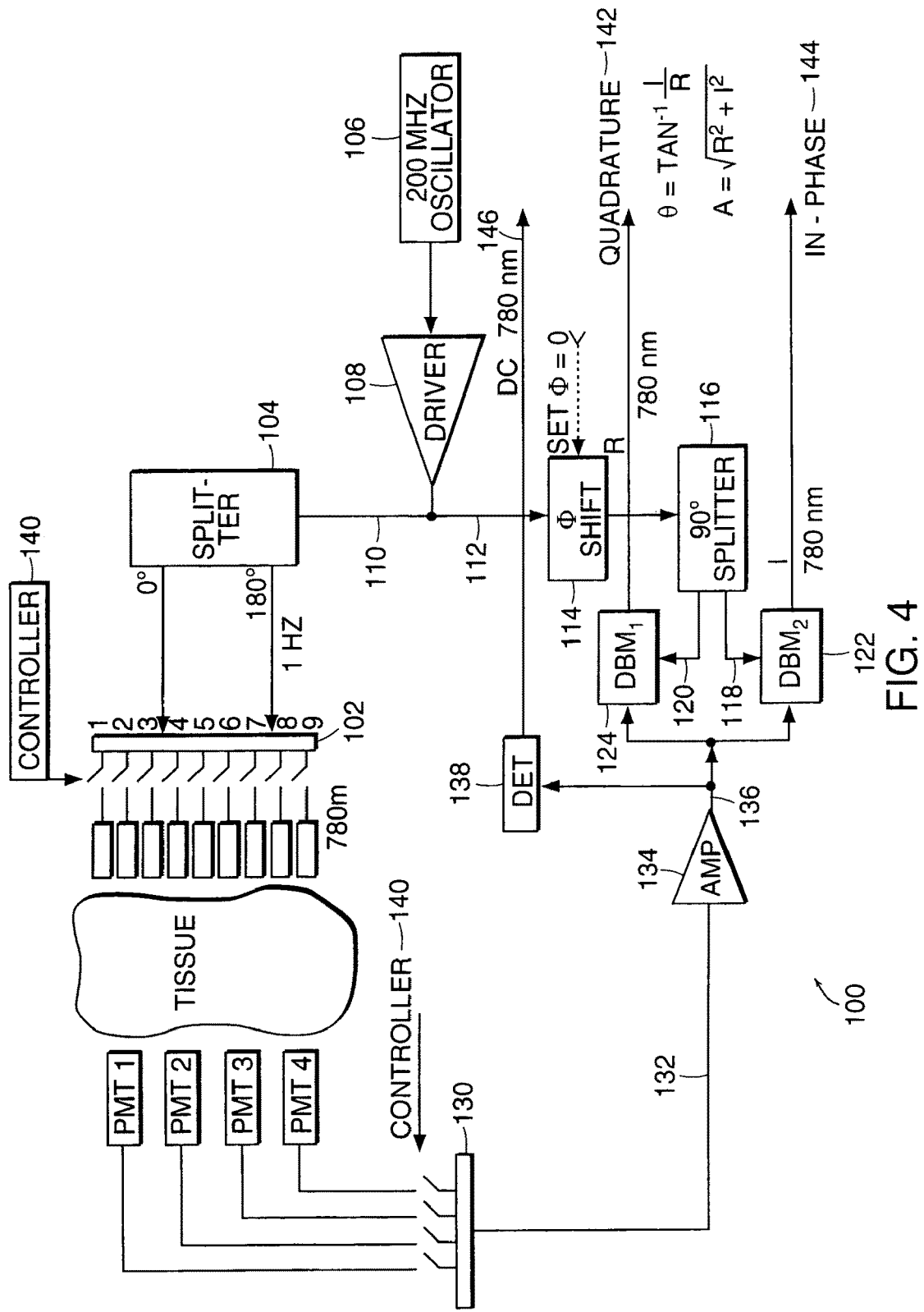

Referring to FIG. 4, in another embodiment, a phased array imaging system 100 is used instead of imaging systems 15 or 45. Imaging system 100, connected to optical module 12 (shown in FIG. 1A) having nine laser diodes $S_1, S_2, \ldots, S_9$ and four PMTs $D_1, D_2, D_3,$ and $D_4$, employs homodyne phase detection. A switch 102 connects laser diodes $S_1, S_2, \ldots, S_9$ to a phase splitter 104, which provides to the diodes an RF modulation signal having both a 0 degree phase and a 180 degree phase. Imaging system 100 also includes a 200 MHZ oscillator 106 providing RF signal to a driver 108, which is connected to phase splitter 104. (Alternatively, an oscillator in the range of 10-1000 MHZ, preferably 50-500 MHZ, may be used.) A phase shifter 14 receives the drive signal (112) from driver 108 and provides the signal of a selected phase (e.g., a 0° phase change) to a 90° phase splitter 116. Phase splitter 116 provides a 0° phase signal (118) and a 90° phase signal (120) to double balance mixers (DBM) 122 and 124, respectively.

A controller 140, connected to a personal computer, sequences laser diodes $S_1, S_2, \ldots, S9$ using switch 102 so that two diodes receive modulate signal at a 0° phase and a 180° phase from splitter 104. At the same time, a controller 140 connects a symmetrically located PMT using a switch 130 to an amplifier 134. Amplifier 134 provides a detection signal (136) to double balance mixers 122 and 124, and to a DC detector 138. Double balance mixer 122 receives the detection signal (136) and the 0° phase reference signal (118) and provides an in-phase signal I (144). Double balance mixer 124 receives the detection signal (136) and the 90° phase reference signal (120) and provides a quadrature signal R (142). DC detector 138 provides DC signal (146). The in-phase signal I and quadrature signal R specify the phase ($\theta$=tan$^{-1}$ I/R) of the detected optical radiation and the amplitude (A =(R$^2$+I$^2$)$^{-1/2}$) of the detected optical radiation. This phase detection circuit was described in U.S. Pat. No. 5,553,614, which is incorporated by reference.

Similarly as for imaging systems 15 and 45, imaging system 100 directs controller 140 to sequence the laser diodes and the PMT detectors using timing diagram 40. The computer stores the phase value and the amplitude value measured for each of the combinations and generates images described below.

FIG. 4A shows diagrammatically one portion of phase cancellation, phased array imaging system 100. The depicted portion of imaging system 100 includes two laser diodes $LD_1$, and $LD_2$ and a lights detector $D_1$, which are included in optical module 12 or 14. Oscillator 106 provides carrier waveform having a frequency in range of 30 to 140 MHz. The carrier waveform frequency is selected depending on the operation of the system. When time multiplexing the light sources using switch 102, then the carrier waveform is modulated at a lower frequency, e.g., 30 MHz to afford switching time.

When no time multiplexing is performed, oscillator 106 operates in the 100 MHz region. Splitter 104 splits the oscillator waveform into 0° and 180° signals that are then lo attenuated by digitally controlled attenuators 107A and 107B by 0% to 10% in amplitude. The phase of the attenuated signals is appropriately shifted by digitally controlled phase shifters 109A and 109B in the range of 10°-30° and preferably 20° in phase. Laser drivers 108A and 108B drive $LD_1$ and $LD_2$, respectively, which emit light of the same wavelength, for example, 780 or 800 nm. After the introduced light migrates in the examined tissued, a PMT detector $D_1$ amplifies the detected signals having initially the 0 and 180° phases. As described above, for homogeneous tissue and symmetric locations of $LD_1$, $LD_2$ and $D_1$, the output of the PMT is 90°, i.e., halfway between 0° and 180° and the amplitude is close to zero. The personal computer (PC) adjusts the attenuation provided by attenuator 107B and the phase shift provided by phase shifter 109B so that detector $D_1$ detects phase nominally around 25° and amplitude nominally around $\leq 10$ millivolts for homogeneous tissue. This signal is connected to amplifier 134 and to the IQ circuit 139. The cosine and sine signals are fed into the personal computer, which takes the amplitude (the square root of the sum of the squares of I and Q) and the phase angle (the angle whose tangent is I/Q) to give outputs of phase around 25° and amplitude signals around 10 millivolts. The personal computer also adjusts the reference signal to the IQ to have the phase $\phi_3$ between 10° to 30° and preferably around 25°, i.e., phase shifter 114 provides to the IQ circuit 139 the reference phase having a value selected by the combination of phase shifters 109A and 109B.

In a currently preferred embodiment, splitter 104 is a two way 180° power splitter model number ZSCJ-2 1, available from Mini-Circuits (P.O. Box 350186, Brooklyn, N.Y. 11235-0003). The phase shifters 109A, 109B and 114 and attenuators 107A, and 107B are also available from Mini-Circuits, wherein the attenuators can be high isolation amplifier MAN-1AD. IQ demodulator 139 is a demodulator MIQY-140D also available from Mini-Circuits.

The system obtains the initial values of attenuator 107B ($A_2$) and phase shifter 109B ($\phi_2$) on a model or a symmetric tissue region (e.g., the contralateral brain lobe that is tumor free). The entire optical probe is calibrated on a tissue model by storing the calibration values of $A_2$ and $\phi_2$ for the various source-detector combinations (i.e., the baseline image). The probe is then moved to the exterior of the head, for example, and the phases and amplitudes are detected for the various source and detector combinations. When the contralateral tumor free brain lobe is used as a model, the probe is transferred to the contralateral lobe (taking note to locate the probe on the symmetrical tissue considering the brain physiology) and then the images are read out from-all the source-detector combinations to acquire the tissue image. There is no limitation on multiplexing as long as the bandwidth of $F_1$ and $F_2$ is recognized as being the limiting condition in the system normalization. It should be noted that normalization must be accurate and without "dither" and therefore, a significant amount of filtering in $F_1$ and $F_2$, i.e., less than 10 Hz bandwidth. If $\phi_2$ is adjusted over a large range, there will be an amplitude-phase crosstalk. Thus, the system may adjust phase and then amplitude and repeat these adjustments iteratively because of the amplitude phase crosstalk. The control of $A_1$ and $\phi_1$ provides even a greater range of control, where obviously inverse signals would be applied to them, i.e., as the $A_1 \phi_1$ signals are increased, the $A_2$, $\phi_2$ signals would be decreased. Both $A_2$ and $\phi_2$ can be controlled by PIN diodes, to achieve an extremely wideband frequency range. However, since signal processing controls the bandwidth of the feedback system, that either PIN diode or relay control of the phase and amplitude is feasible for automatic compensation. If, in addition, dual wavelength or triple wavelength sources are used, each one of them must be separately calibrated because no two light sources can be in the same position relative to the imaged tissue (unless, of course, they are combined with optical fibers).

Figure 5:
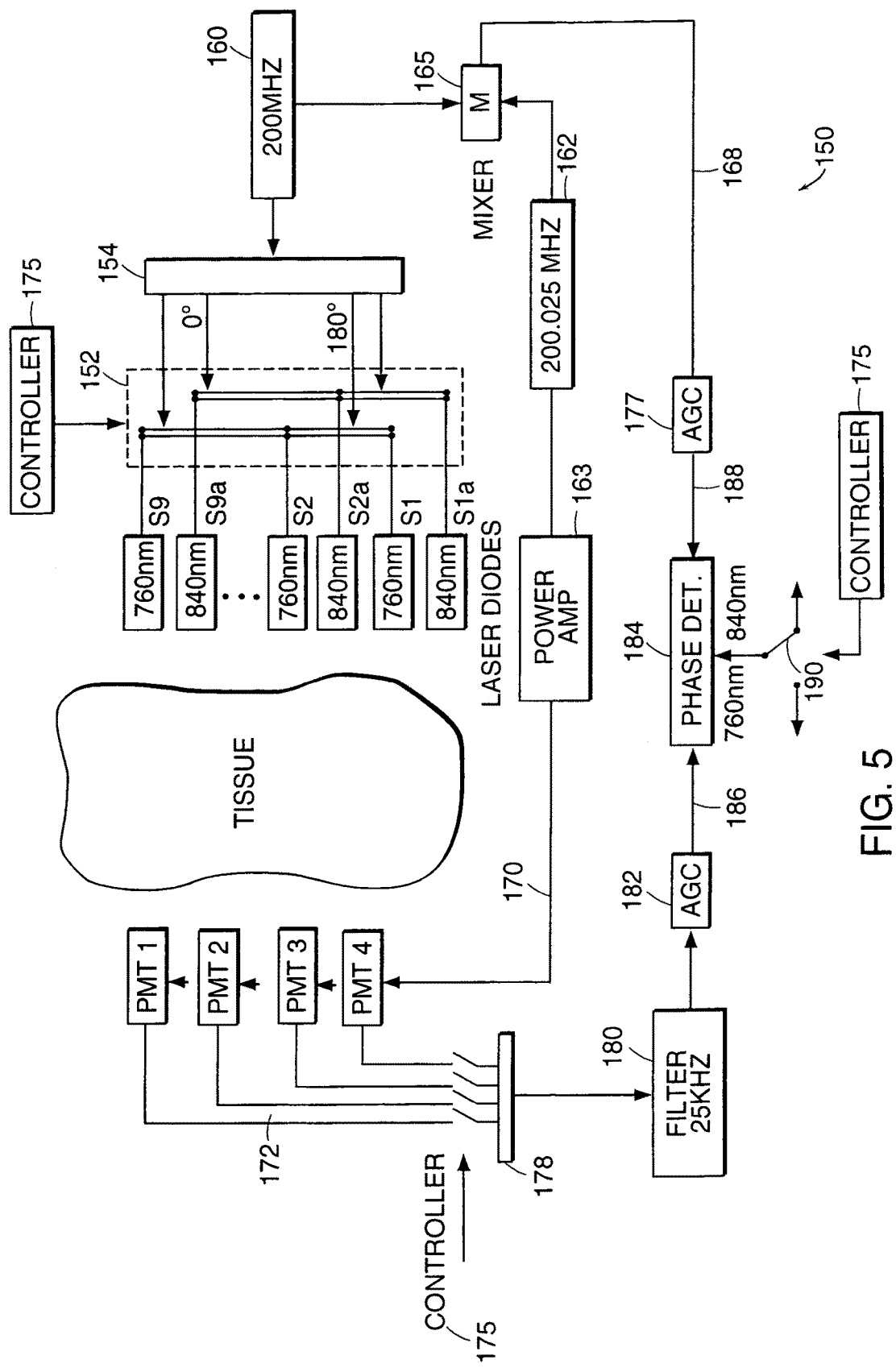
FIG. 5 shows diagrammatically another embodiment of the phase cancellation imaging system employing the optical module of FIG. 1A or FIG. 2A.

Referring to FIG. 5, in another embodiment, a dual wavelength phased array imaging system 150 is used instead of imaging systems 15, 45 or 100. Imaging system 150, connected to optical module 12 (shown in FIG. 1A) having nine 760 nm laser diodes $S_1, S_2, \ldots, S_9$, nine 840 nm laser diodes $S_{1a}, S_{2a}, \ldots, S_{9a}$ and four PMTs $D_1, D_2, D_3$, and $D_4$ is based on heterodyne phase detection. A switch 152 connects the laser diodes to a phase splitter 154, which provides to the diodes an RF modulation signal having both a 0 degree phase and a 180 degree phase. Imaging system 150 employs a mixer 165 connected to a 200 MHZ oscillator 160 and 200.025 MHZ oscillator 162 (Alternatively, oscillators operating in the range of 10-1000 MHZ, preferably 50-500 MHZ, may be used.) Mixer 165 provides a 25 kHz reference signal (168) to an adjustable gain controller 177. Oscillator 162 connected to power amplifier 163 provides a 200.025 MHZ reference signal (170) to the second dynode of each PMT detector for heterodyne detection. Each PMT detector provides a 25 kHz detection signal (172) to a switch 178, which in turn provides the signal to a 25 kHz filter 180. A phase detector 184 is connected to an adjustable gain controller 182, which provides a filtered and amplified detection signal (186) and to adjustable gain controller 177, which provides the reference signal (188). Phase detector 184, connected to a switch 190, provides the detected phase value for each wavelength. This phase detection circuit was described in U.S. Pat. No. 5,187,672, which is incorporated by reference. Another type of phase detection circuit was described in U.S. Pat. No. 5,564,417, which is incorporated by reference.

Similarly as described above, controller 175, connected to a personal computer, sequences laser diodes $S_1, S_2, \ldots, S_9$ or laser diodes $S_{1a}, S_{2a}, \ldots, S_{1a}$ using switch 152 so that two diodes emitting the same wavelength receive 0° phase and 180° phase signals from splitter 154. At the same time, controller 175 connects a symmetrically located PMT using a switch 178 to filter 180 and adjustable gain controller 182. Phase detector 184 provides the measured phase. Imaging system employs timing diagram 40 (FIG. 3B); however, since the two wavelength light is not frequency encoded, laser diodes $S_1, S_2, \ldots, S_9$ or laser diodes $S_{1a}, S_{2a}, \ldots, S_{9a}$ are triggered in each sequence. The computer stores the phase values measured for the different combinations and generates images described below.

Figure 6:
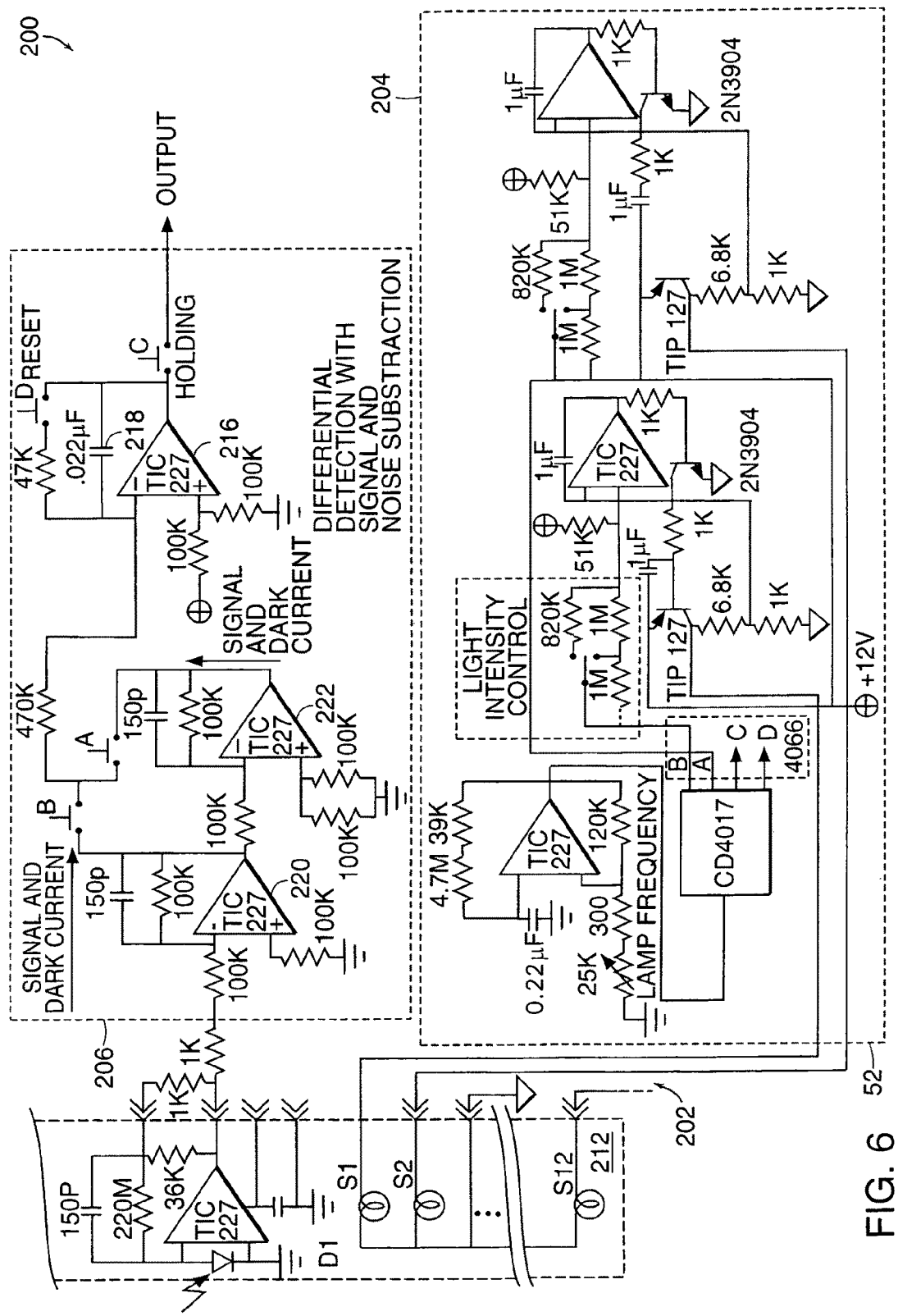
FIG. 6 shows schematically an amplitude cancellation imaging system.
Figure 6A:
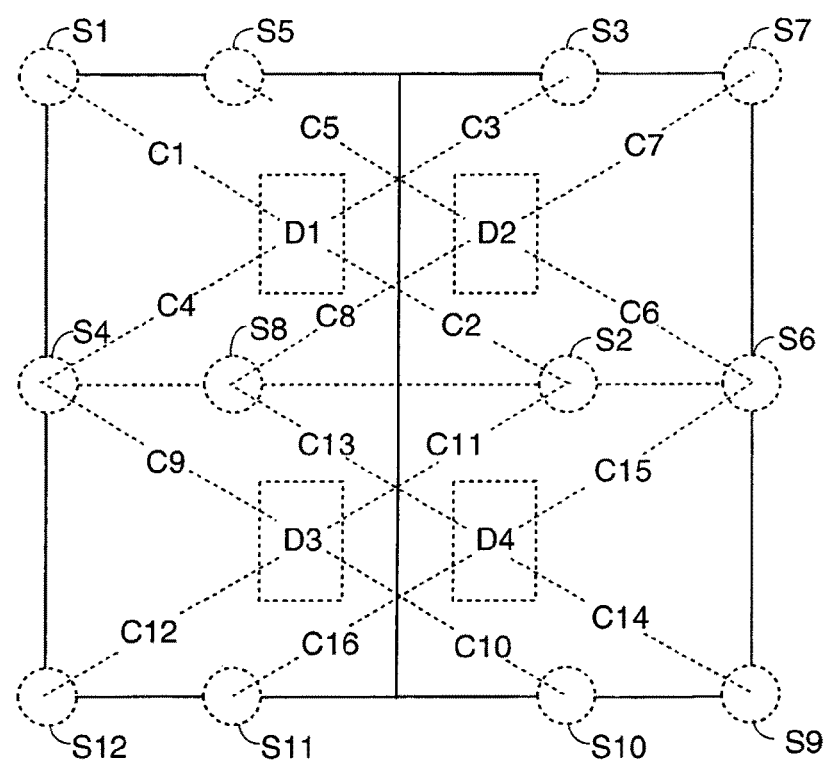
FIG. 6A shows another embodiment of the optical module used with the imaging system shown in FIG. 6.

Referring to FIG. 6, in another embodiment, an amplitude cancellation imaging system 200 uses an optical module 212 shown in FIG. 6A. Optical module 212 includes twelve light sources S1, S2, ..., S12 and four light detectors D1, D2, D3, and D4 mounted on a plastic or rubber foam material. The light sources and the light detectors are located on a geometrical pattern that provides sixteen source-detector combinations (C1, C2, . . . , C16) having a selected source-detector separation. The separation may be 2.5 cm to produce about 1.25 cm average light penetration. (Several modules with different source-detector separations may be used to obtain several two dimensional images of different tissue depths. Alternatively, a single module may include source detector combinations providing different separations.) The light sources are 1 W tungsten light bulbs, which emit broad band non-modulated light. The light detectors are silicon diodes, each equipped with an interference filter transmitting a 10 nm wide band centered at 760 nm and 850 nm. The 760 nm and 850 nm wavelengths are selected to detect oxyhemoglobin and deoxyhemoglobin in the examined tissue.

Optical module 212 is connected to an analog circuit 202, which includes a source circuit 204 for controlling sources S1, S2, . . . S12. Optical module 212 is connected to a detector circuit 206, which controls diode detectors D1, D2, D3 and D4. In general, imaging system 200 can turn ON each source for a selected period in the range of $10^{-6}$ sec. to 0.1 sec., and one or several symmetrically located detectors are turned on simultaneously or sequentially to collect optical data. Specifically, as provided in Appendix B, one of sources S1, S2, . . . S12 is turned ON for 500 msec and the emitted light is introduced into the tissue from the corresponding input port. The introduced photons migrate over banana shaped paths in the examined tissue to a detection port. The corresponding detector is triggered 200 msec. after the source and collects light for 200 msec. Detector circuit 206 receives a detector signal from the diode detector. Detection circuit 206 enables correction for the dark current/noise that comprises background light, DC offset of the operational amplifiers, photodiode dark current, temperature effects on the outputs of individual components and variations due to changing environment.

Imaging system 200 performs data acquisition in four steps synchronized by its internal oscillator. The first step is performed by having the light sources OFF. The detector output is directed to an intergrator 216 and integration capacitor 218 is charged to the dark level voltage. In the second step, the light source is turned ON and after 200 msec the preamplifier output that corresponds to the intensity of the detected light is directed to intergrator 216 in a way to charge capacitor 218 with current of polarity opposite to the polarity of the charging current in the first step. This is achieved using an appropriate ON/OFF combination of switches A and B. The voltage of capacitor 218 is charging to a value that, after 200 msec., represents the total detected intensity minus the dark level noise signal. In the third step; both switches A and B are turned OFF to disconnect both the positive unity gain and the negative unity gain operational amplifiers (220 and 222). Then, the output of integrator 218 is moved via switch C to an analog-to-digital converter and the digital signal is stored in the memory of a computer. In the fourth step, the switches A, B and C are open and switch D is closed in order to discharge capacitor 218 through a 47K resistor. At this point, the circuit of intergrator 216 is reset to zero and ready for the first step of the detection cycle.

Alternatively, analog circuit 202 may be replaced by a computer with an analog-to-digital converter and appropriate software that controls the entire operation of optical module 212. An algorithm controls the sources and the detectors of optical module 212 in a similar way as described above. The detected dark level noise signal is digitally subtracted from the detected intensity of the introduced light.

The collected data sets are processed using an imaging algorithm. The imaging algorithm calculates the blood volume of the examined tissue for each source-detector combination for each data set. The imaging algorithm can also calculate the oxygenation of the examined tissue for each source-detector combination.

The blood volume or oxygenation images can be subtracted from "model" images. The blood volume image can be subtracted from the oxygenation image to create congruence data to localize and characterize a tissue anomaly. That is, the imaging algorithm creates an image using the differential image data sets. Prior to creating the image, an interpolation algorithm is employed to expand the differential image data set, containing 16 (4×4) data points, to an imaging data set containing 32×32 image points.

Alternatively, the computer uses a back-projection algorithm known in computed tomography (CT) modified for light diffusion and refraction and the banana like geometry employed by the optical imaging system. In the optical back-projection algorithm, the probabilistic concept of the "photon migration density" replaces the linear relationship of ballistically transmitted X-rays, for the beam representing pixels. The photon migration density denotes a probability that a photon introduced at the input port will occupy a specific pixel and reach the detection port. For different types of tissue, the phase modulation spectrophotometer provides the values of the scattering and absorption coefficients employed in the probability calculations. In the image reconstruction program, the probability is translated into a weight factor, when it is used to process back-projection. A back-projection algorithm known in X-ray CT may be used. The back-projection averages out the values of information that each beam carries with the weighting in each pixel. A weighting algorithm for creating a photon density image may be used in the back-projection reconstruction algorithm mentioned above.

A method for correcting blurring and refraction used in the back-projection algorithm was described by S. B. Colak, H. Schomberg, G. W. 't Hooft, M. B. van der Mark on Mar. 12, 1996, in "Optical Back-projection Tomography in Heterogeneous Diffusive Media" which is incorporated by reference as if fully set forth herein. The references cited in this publication provide further information about the optical back-projection tomography and are incorporated by reference as if fully set forth herein.

Another embodiment of the amplitude cancellation imaging system 200 uses optical module 14 shown in FIG. 2A. In this arrangement, four centrally located light sources S1, S2, S3, and S4 and 21 detectors D1, D2, . . . , D21 provide a multiplicity of symmetric photon migration paths for each source. For example, source S1 is turned ON for a period in the range of $10^{-6}$ sec. to 0.1 sec. The source emits non-modulated light into the examined tissue. Symmetrically located detectors D1 and D11 are ON simultaneously to collect introduced photons migrating over substantially symmetric paths. For normal brain tissue, detectors D1 and D11 detect light of the same intensity, and thus the differential signal is zero, i.e., the detected amplitude are canceled. Imaging system 200 collects the differential data for a multiplicity of symmetric photon migration paths and generates an image of the examined tissue. Imaging system 200 may collect optical data for several wavelengths and generate blood volume images and blood oxygenation images for the examined tissue. Amplitude cancellation imaging system 200 may also use a second identical optical module 14 placed to examine a symmetrical brain region, for example, the opposite lobe of the brain. The blood volume or oxygenation images collected for the two symmetric brain regions may be subtracted to provide a differential image, which will further emphasize a tissue abnormality located in one brain region.

Alternatively, the amplitude cancellation imaging system uses light modulated at frequencies in the range of 0.1 to 100 kHz. The system employs the above-described algorithm, but the light sources emit frequency modulated light and the detectors, each connected to a lock-in amplifier, detect light modulated at the same frequency. This lock-in detection may further increase the signal to noise ratio by eliminating external noise. The detected light intensities are processed the same way as described above to image the examined tissue.

Figure 7:
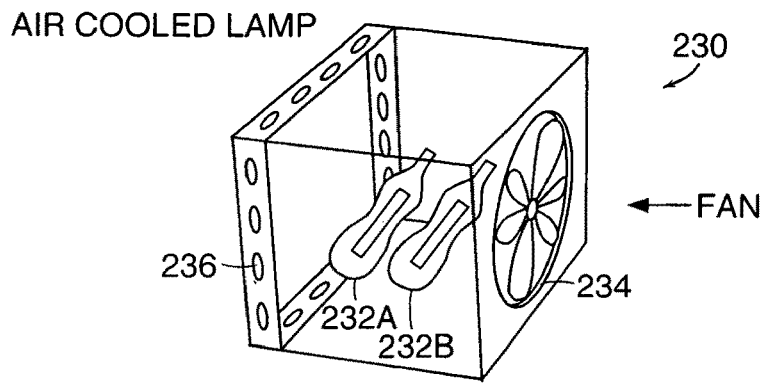
FIGS. 7, 7A and 7B show different embodiments of a cooling module used with a broad band light source such as a tungsten light bulb.
Figure 7A:
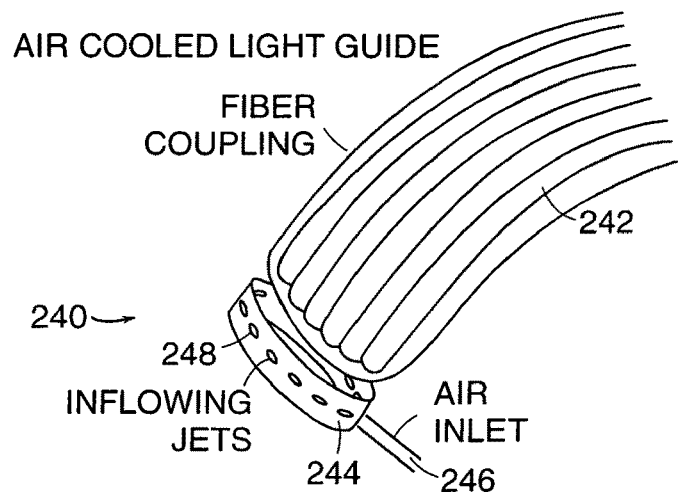
Figure 7B:
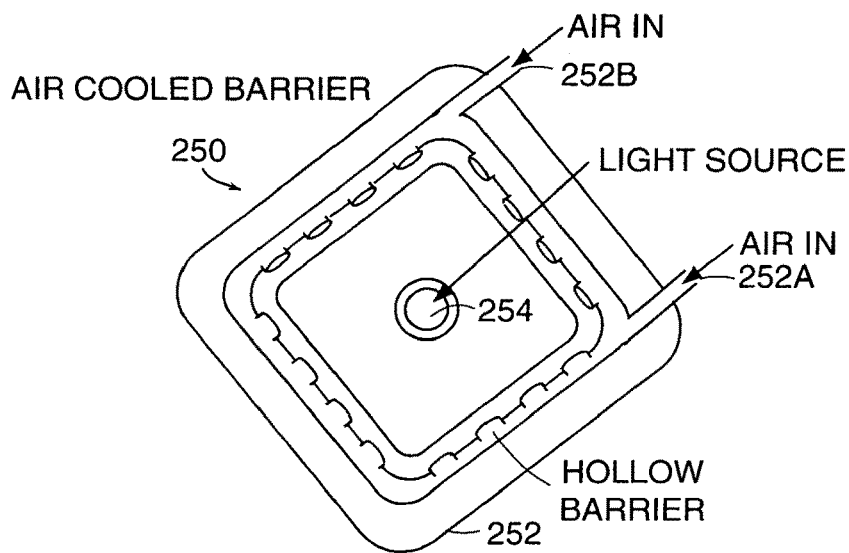

FIGS. 7, 7A and 7B show different embodiments of a cooling module used with a broad band light source or light guides, where they are positioned close to the skin. In this arrangement, there is trapped heat that frequently causes an uncomfortable temperature. FIG. 7 depicts a cooling module 230, which surrounds light sources 232A and 232B. Cooling module 230 includes a fan 234 and a set of air passages 236. In a similar design, two fans are juxtaposed on each side of one or more light bulbs to form an "open frame" so that the fans blow not only upon the light sources, but upon the skin itself. The cooling module enables a power increase on the light sources, but no increase of heat upon the skin itself, which remains under comfortable conditions.

FIG. 7A depicts a cooling module 240 for cooling light guides. Light guides 242 deliver light and heat to the skin. A cooling ring 244 includes an air inlet 246 and a set of air passages 248 (or jets) for providing air flow to the irradiation location. FIG. 7B depicts a cooling module 250 constructed to air cool a light barrier 252. Light barrier 252 has similar optical properties as the light barrier described in the PCT application PCT/US92/04153 (published on Nov. 26, 1992 as WO 92/20273), which is incorporated by reference. This embodiment utilizes the advantages of the light barrier and enables the use of higher light intensities. Cooling module 250 includes air inlets 252A and 252B, which provide air to a set of conduits and openings that deliver air to the skin near light source 254. Compressed air may also be used.

Figure 8:
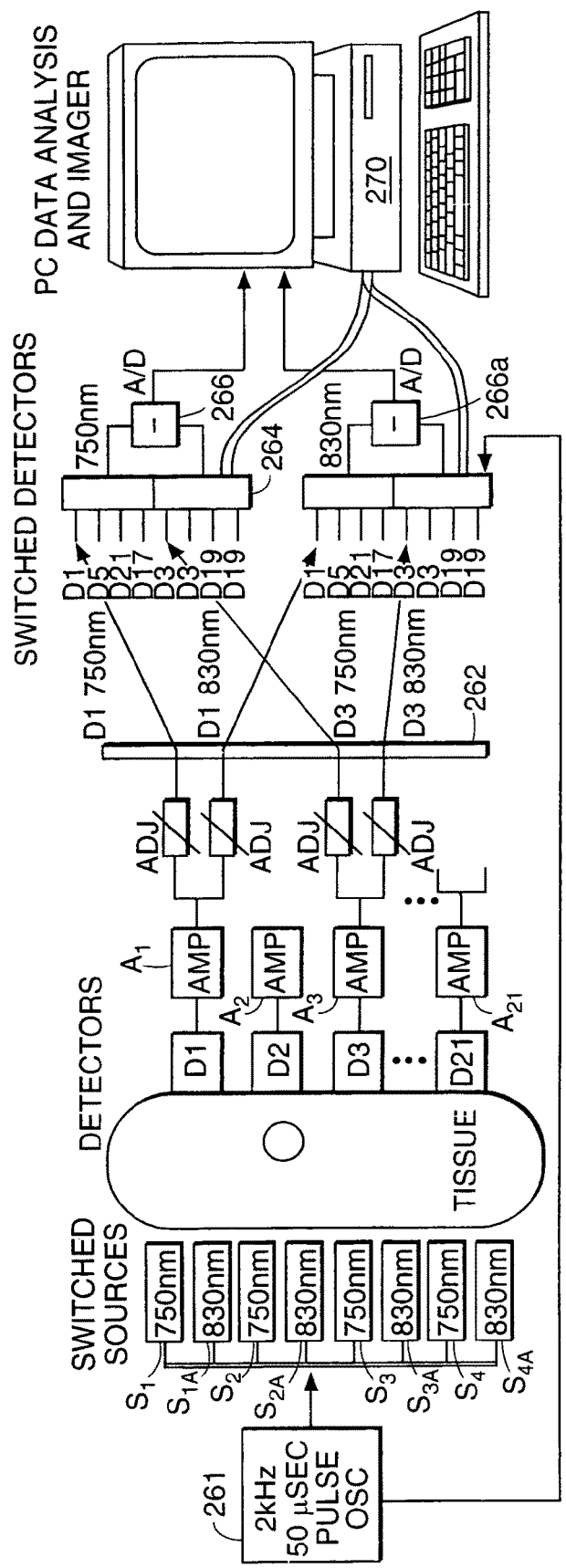
FIG. 8 shows diagrammatically another embodiment of the amplitude cancellation imaging system employing the optical module of FIG. 2A.

The intensity regulations for delivering continuous otherwise noncoherent light to the skin often depend on the temperature rise of the skin itself. For examination of large tissue volumes or deep tissues (i.e., where there is a large separation between the optical input and optical detection ports) relatively large light intensities are needed. Under conditions of prolonged even low level illumination, the skin may become uncomfortably warm and may blister. However, the erythemic effects are much smaller in the NIR, where the delivered heat is a factor, than they are in UVA and UVB, where cancer-producing damage may occur (but is not known for the NIR). The effect of the cooling air is not just convection of warm air away from the skin, but it enhances the evaporation of perspiration from the skin. Thus, as soon as the skin temperature rises and perspiration is initiated, greatly enhanced cooling is obtained with the forced air increasing the evaporation Referring to FIG. 8, an amplitude cancellation imaging system 260 is used instead of imaging systems 15, 45, 100, 150, or 202. Dual wavelength amplitude cancellation imaging system 260 is connected to optical module 14 shown in FIG. 2A and includes four 750 nm laser diodes $S_1$, $S_2$, $S_3$, and $S_4$, four 830 nm laser diodes $S_{1a}$, $S_{2a}$, $S_{3a}$, and $S_{4a}$, and twenty silicon diode detectors $D_1$, $D_2$, . . . , $D_{21}$. Each detector is connected to a preamplifier and an adjustable gain controller that may be used initially for calibration. The detector outputs are switched by a switch 262 by a controller 264 so that analog-to-digital converters 266 and 266a receive 750 nm and 830 nm data, respectively, from two symmetrically located detectors. A computer 270 stores the detected values measured for the different combinations using algorithms employed by the enclosed source code. The computer also generates images described below. Another type of amplitude detection circuit was described in FIGS. 11 through 13 and the corresponding specification of U.S. Pat. No. 5,673,701, which is incorporated by reference as if fully set forth herein.

Figure 8A:
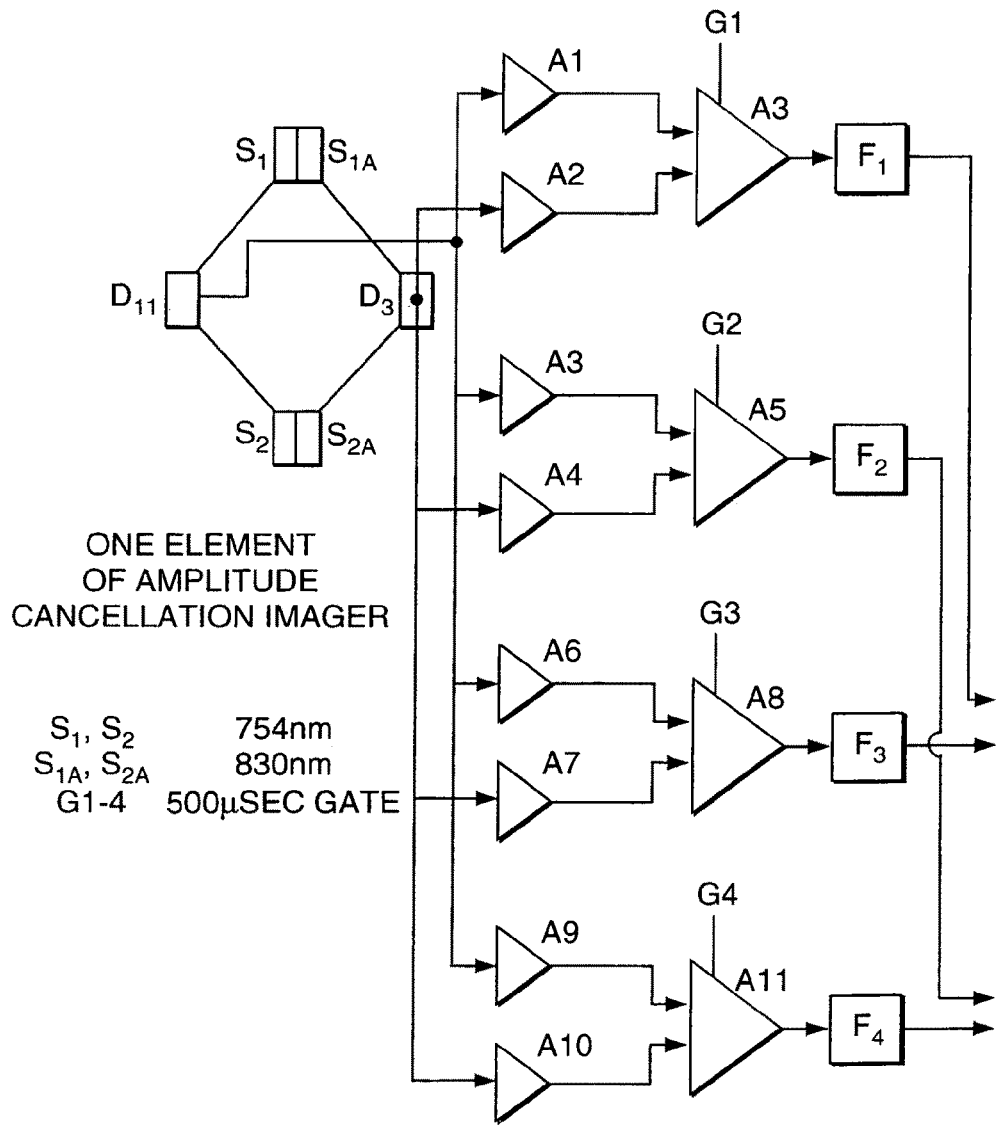
FIG. 8A shows a circuit configuration for one element of the amplitude cancellation imaging system of FIG. 8.
Figure 8B:
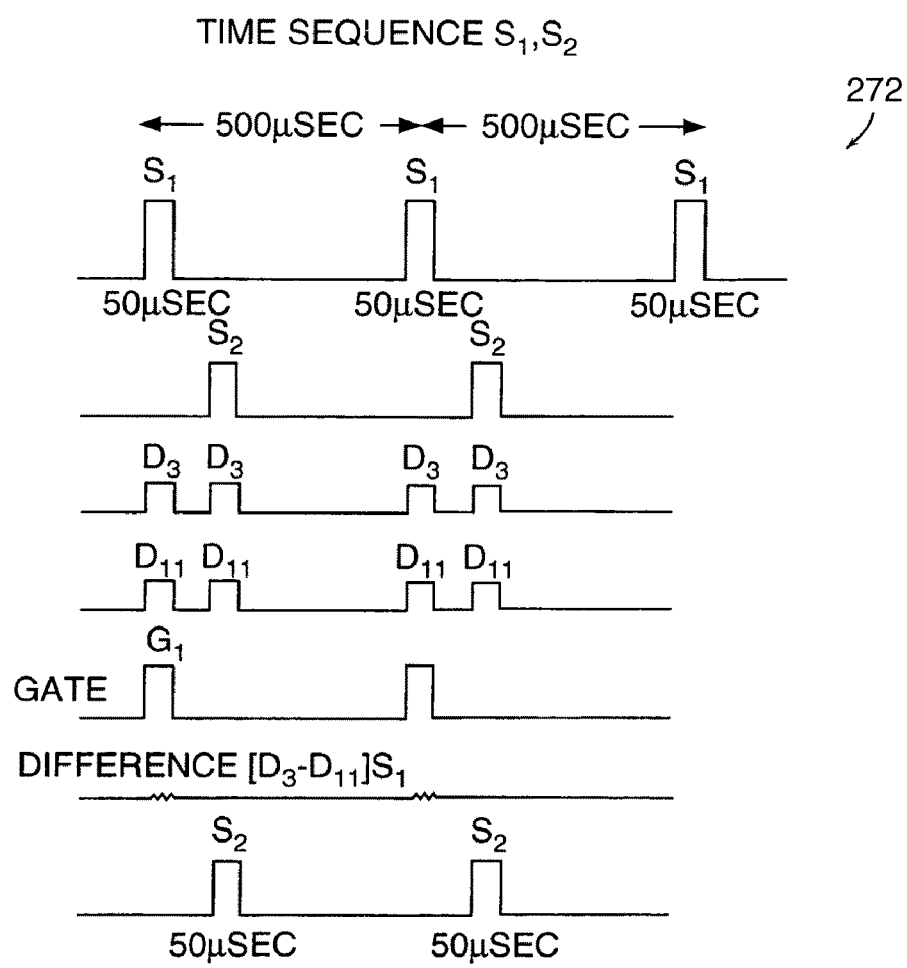
FIG. 8B is a timing diagram used by the imaging system of FIG. 8.

Also referring to FIGS. 8A and 8B, the controller sequences an oscillator 261 so that each source emits a 50 μsec light pulse as shown in timing diagram 272. The system sequences through the various source/detector combinations in approximately one msec, and averages the imaged data over 8 sec to get a very high signal to noise ratio. The circuit configuration for one element of imaging system 260, i.e., 754 nm sources $S_1$, $S_2$ and 830 nm sources $S_{1a}$, $S_{21}$, and two symmetrically positioned detectors $D_3$ and $D_{1a}$, is shown in FIG. 8A. The light intensities detected for the symmetrical locations are subtracted in a digital or analog way. The computer stores all data detected for the two wavelengths for generating tissue images.

Figure 8C:
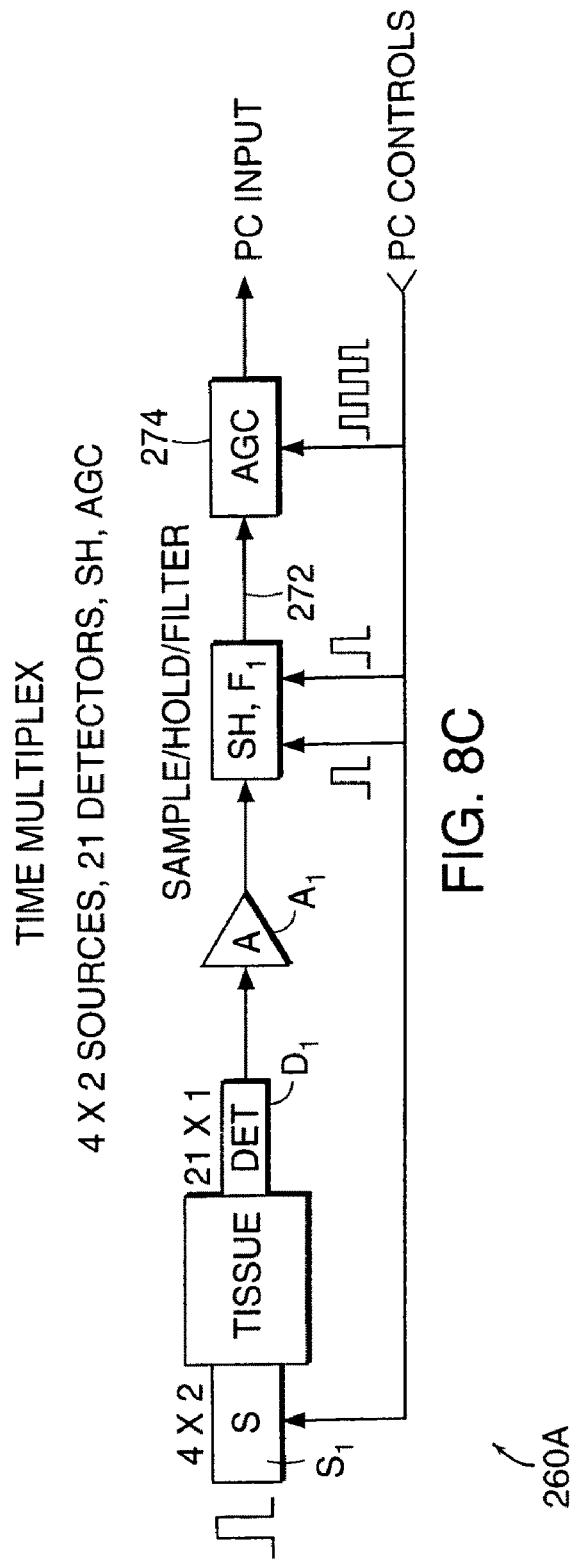
FIG. 8C shows diagrammatically one channel of the amplitude cancellation imaging system of FIG. 8.

FIG. 8C shows diagrammatically a single channel 260A of the time multiplex imaging system 260. Detector $D_1$ detects light emitted from light source $S_1$ emitting light pulses of the duration of about 50 μsec. The detector signal is amplified and provided to a sample-and-hold circuit and filter. Detector $D_1$ is a silicon diode detector that has the detection area of about 4×4 mm and includes a pre-amplifier. The filtered signal 272 is provided to an AGC 274, which adjusts the amplitude of the signal based on a control signal from a personal computer. The personal computer has normalization amplitudes for the individual source-detector combinations.

Amplitude cancellation imaging system 260 is normalized on a tissue model by detecting signals for the individual source-detector combinations and appropriately normalizing the detected signal using the AGC control. The individual normalization/calibration amplitudes form a baseline image that is stored in the computer. As described above, the baseline image may also be acquired on a symmetric tissue region, such as the contralateral brain tissue for brain tissue examination, or the contralateral tissue in general for any tissue examination. The normalization process can be repeated several times to account for drifts in the individual elements. During the measurement process, the personal computer can adjust the gain of each AGC 314 based on the calibration values that account only for the electronic drift. Then, the defected image is subtracted from the baseline image of the examined tissue. Alternatively, while collecting the measurement data on the examined tissue, the measurement image is subtracted from the baseline image to create the tissue image that includes any tissue in homogeneities such as a tumor or bleeding. The sample-and-hold circuit maybe an analog circuit or the sample-and-hold function, including the filtering, may be performed digitally.

Figure 8D:
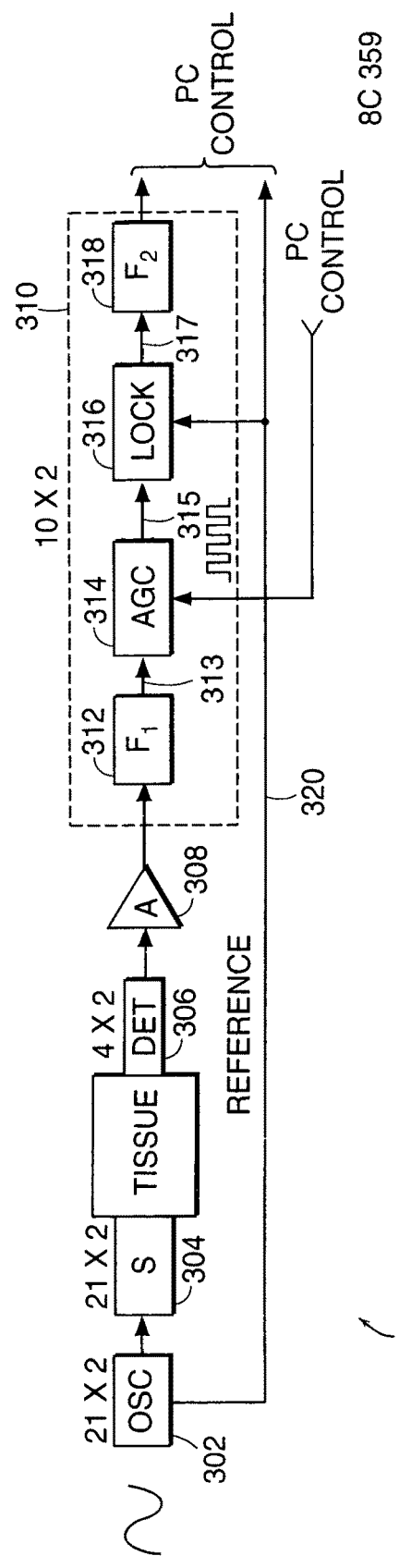
FIG. 8D shows diagrammatically another embodiment of the amplitude cancellation imaging system of FIG. 8.

FIG. 8D shows diagrammatically an amplitude cancellation imaging system employing a frequency multiplex method. Amplitude cancellation system 300 includes 21 oscillators 302 operating a frequencies in the range of 1 kHz to 100 kHz. Each oscillator 302 drives a light source 304 (for example, a laser diode or LED), which emits an intensity modulated light into the examined tissue. Each light detector 306 (for example, a photomultiplier, an avalanche photodiode PIN detector or a silicon detector) detects the intensity modulated light and provides a detector signal to an amplifier 308. The amplified detector signal is provided to a processing channel 310, which includes a band pass filter 312, an AGC 314, a lock-in amplifier 316, and a filter 318. Filter 312 filters the detector signal, and AGC 314 adjusts the amplitude according to the input signal from a personal computer. Lock-in amplifier 316 receives the amplified signal 315 and a reference signal 320 from oscillator 302. Lock-in amplifier 312 provides amplitude signal 317 to filter 318. Processing channel 310 may be an analog channel or a digital channel.

In the amplitude cancellation system 310, all light sources emit light at the same time into a selected tissue region. Each light source is modulated at a distinct frequency in the range of 1 kHz to 100 kHz. In order to resolve the modulated light signals and attribute them to the individual light sources, the oscillators operate at frequencies 1 kHz, 2 kHz, 4 kHz, 8 Hz, 16 kHz, . . . Filters 312 and 318 are designed to provide only the detection signal from a elected light source, and lock-in amplifier 312 provides the amplitude of the signal at the selected frequency. Frequency multiplex system 300 is calibrated the same way as the time multiplex system 260, and the normalization/calibration amplitude values are also stored in the personal computer. The images are processed as described above.

All above-described imagers will achieve a higher spacial resolution of the imaged tissue by increasing the number of sources and detectors. Furthermore, the sources and detectors may form various 1 dimensional, 1.5 dimensional, or 2 dimensional arrays as described in the above-referenced documents.

Before examination of a selected brain region, the imager is first calibrated on a brain model. During the examination, the patient or the attendant holds optical probe 12 over a designated portion of the head. The mirror image region on the contralateral brain region may also be recorded. The images can be acquired by taking advantage of a priori information obtained by X-ray tomography, an MRI or PET scan. The optical images were created using a back-projection algorithm with or without correction for non-ballistic photon propagation (i.e., tissue absorption or scattering) as provided in Appendix A-5. The images may be displayed in the format of the left brain hemisphere data minus the model data, the right brain hemisphere data minus the model data, for each wavelength (e.g., 750 and 830 nm). Alternatively, the model calibration may be performed by adjusting the detector gains prior to the brain tissue measurements. Furthermore, the images may be the differential between the right brain region and the left brain region, for each wavelength, to emphasize any tissue difference, such as a suspicious structure, which is unlikely located symmetrically in both brain regions.

The optical images may also be processed to image blood volume and blood oxygenation of the examined tissue of each brain region. The blood volume image is the sum of 0.3 times the 750 nm data and 1.0 times the 830 nm data. The blood deoxygenation image is the difference of the 750 nm and the 830 nm data. The above coefficients were derived from blood tests in model systems. The images have the highest specificity and sensitivity when the contralateral brain region data is used as a baseline and both the blood volume data and the hemoglobin deoxygenation data is imaged and positionally compared.

The blood volume and hemoglobin deoxygenation images provide an important tool in characterizing a suspicious anomaly in the examined brain. While the blood volume and hemoglobin deoxygenation images, as well as the single wavelength images, are useful in locating an abnormal tissue region (i.e., detecting the abnormal structure), these images are also used to characterize the metabolism or pathology of the suspicious tissue anomaly. Specifically, an increased blood volume signal is observed with respect to the adipose tissue background due to the increased vascularity of a tumor as a consequence of angiogenetic factors. These factors include actively metabolizing regions and necrotic/apoptotic regions of the tumor. On the other hand, the hemoglobin deoxygenation signal is related to metabolic intensity. That is, the balance between oxygen delivery and oxygen uptake, which in tumors is usually balanced in favor of oxygen uptake exceeding oxygen delivery. The increased oxygen uptake occurs particularly for those tumors that are aggressively growing, and may as well be metastatic.

By selecting an appropriate wavelength, or several wavelengths, sensitive to an optically active tissue property, the imaging system can non-invasively characterize a tissue anomaly. The above-mentioned wavelengths are sensitive to hemoglobin and hemoglobin oxygenation, but other wavelengths sensitive to absorption by any tissue constituent may be used. Furthermore, an optical contrast agent (e.g., cardiogreen, indocianine green) may be injected intravenously. The imaging system will then use a wavelength sensitive to the administered contrast agent. The regions of increased blood volume will also have a higher content of the contrast agent.

Alternatively, differences in tissue scattering may be imaged. Due to differences in the optical refractive index, different types of tissue and different tissue solutes scatter light differently. The above-described imaging systems are also sensitive to scattering changes. The imaging system may use a wavelength that does not exhibit absorption changes for different types of tissue and different tissue solutes, but exhibits differences in scattering.

The non-invasive characterization of the brain tissue may be performed by combining the data from the above described images. For example, a two dimensional data chart may display blood volume (i.e., vasculogenesis) vs. blood deoxygenation (i.e. hypermetabolism) for a "suspicious structure" using the contralateral brain region data as a reference, or using the model data as a reference.

Quantitation of Co-registration of Several Images

In principle, vasculogenesis (blood volume) and hypermetabolism (tissue hypoxia) occur in similar and often identical tissue volumes. The vascular volume signal can be reinforced by the blood volume signal. I can evaluate the congruence of the two images in order to further reinforce the identity of a suspicious region, for example, by quantitation of the congruence evaluated pixel by pixel. The first step is the normalization of the two images to equalize the maximum signals. Appropriate computer programs exist for selecting the area and obtaining the integrated value for the spatial congruence residual and for the blood volume signal. Then, subtraction pixel-by-pixel gives an image that provides a residual on which to base an estimate of the congruence of the two shapes, blood volume and deoxygenation. This has been carried out for those shapes which appear by inspection to be congruent and the integral of the residual non-zero pixels is compared to the total signal. A simpler procedure is to take the maximum value of the difference and divide it by the maximum value of the normalized value for the two images.

Figure 9:
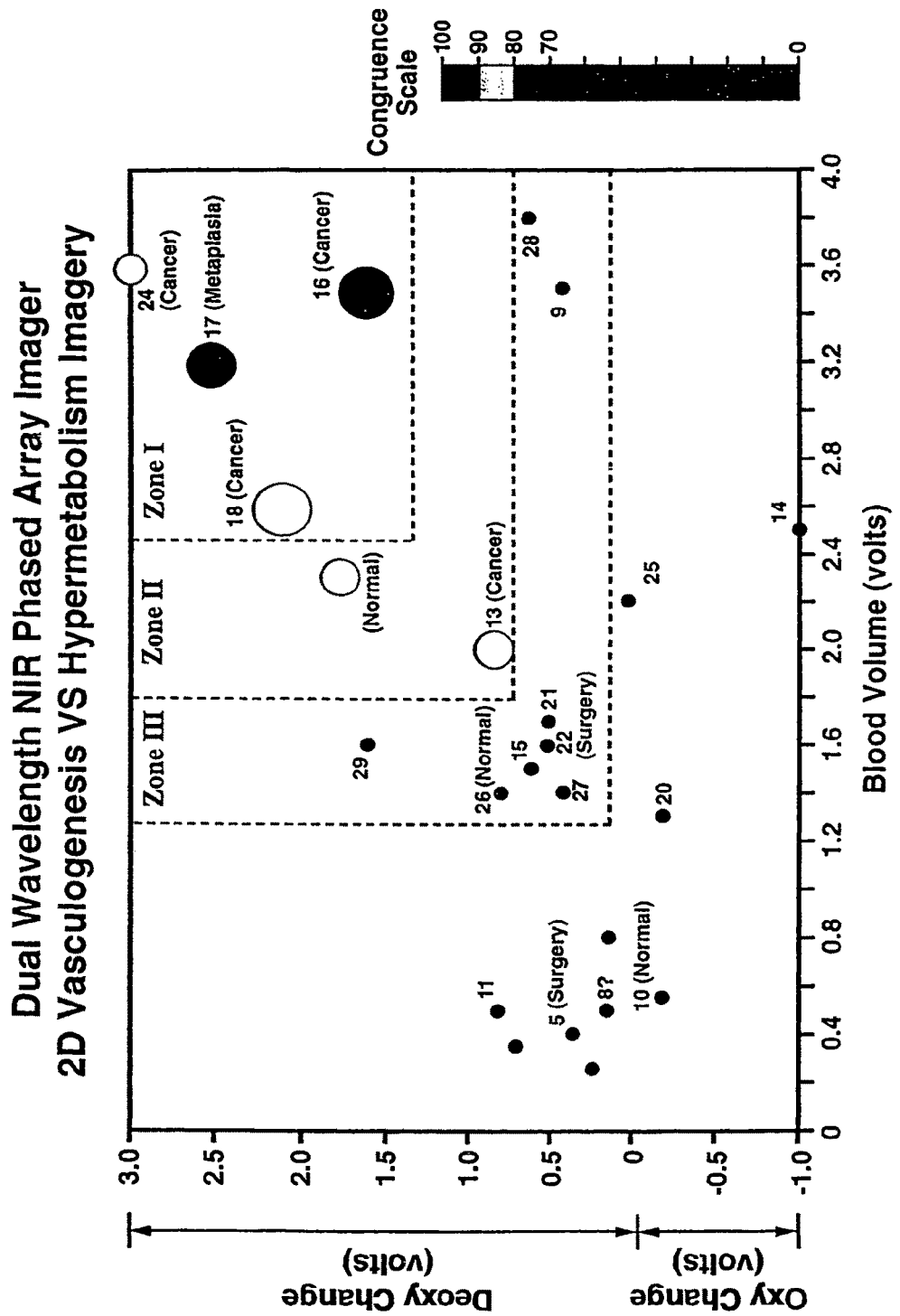
FIG. 9 is an example of a "four" dimensional graph that could be used to summarize optical examination of suspicious masses.

Referring to FIG. 9, a "four" dimensional graph may be used to summarize images of suspicious regions (FIG. 9 is only a hypothetical summary and not actual brain tissue data). The blood volume (Volts) is plotted on the abscissa and deoxygenation (Volts) on the ordinate. The measured size of image is depicted as the circle diameter and the percentage congruence between the blood volume image and the deoxygenation image is shown by a color scale. Color coding the percentage of congruence signals may be given a color scale based on the following formula:

$$1 - \left(\frac{\text{maximum overlap residual}}{\text{maximum blood volume signal}}\right) \times 100$$

The "four" dimensional diagram is summarized as follows:
1. The size of the image of suspicious mass (plotted as one half its longest dimension).
2. The congruence of blood volumes and blood deoxygenation plotted in a color.
3. The blood volume in the congruent region measured in volts (scale of the abscissa).
4. Blood deoxygenation in the congruent region (scale of the ordinate).

A brain model was constructed to test the above-described imaging techniques and calibrates the imaging systems. The model included a 4×8×8 millimeter cellophane chamber connected to a source of oxygenated or deoxygenated blood. The chamber was placed 2.5 cm deep within the solid brain model with the absorption coefficient $\mu_a$=0.04 cm$^{-1}$, and the scattering coefficient $\mu_a'$=10 cm$^{-1}$. The chamber was filled with blood of appropriate concentrations and could be moved to various positions within the model. An accurate determination of relative changes of blood concentration was obtained in error of 2 µM from 50 to 160 µM (covering the physiological range). The position errors of ±12 mm was determined by comparing the image obtained from the back-projection algorithm with the real position. The phased array system has shown a very high positional accuracy and object detection at a depth of 3 cm.

Functional Imaging

In another important embodiment of the invention, the above-described imaging systems are used to image the functional activity of a selected brain region. The functional imaging alone, or in combination with the above described structural imaging or tissue characterization imaging, detects a brain anomaly. A functional imaging system includes one of the above described optical imaging systems and a stimulation unit that is constructed to stimulate a specific neural function of the examined subject. The optical module is placed to examine the stimulated tissue region (for example, on the parietal bone of the skull to observe the surface of the parietal cortex). The stimulator, operating in unity with the imaging system, emits mechanical, electrical, thermal, sound or light signals designed to stimulate selected neural activity in the tissue region probed by visible or infrared light. The neural activity is induced by sensory stimuli, such as visual, auditory, or olfactory stimuli, taste, tactile discrimination, pain and temperature stimuli, or proprioceptive stimuli. The functional imaging is also described in U.S. Pat. No. 5,853,370 issued Dec. 29, 1998, which is incorporated by reference as if fully set forth herein.

The functional imaging can examine and image numerous centers of the neural activity. For example, the optical module may be attached to the temporal bone of the skull to examine the surface of the temporal lobe. Then, the stimulator stimulates the auditory function while the optical tomography system images neurofunctional activity of the auditory area of the temporal lobe. The optical system may also image the auditory association cortex of Wernicke in the temporal lobe before and after stimulation by the stimulator.

Another neurofunctional examination includes placing the optical module to the frontal bone of the skull to examine the frontal lobe. Then, the stimulator stimulates the motor speech function while the optical tomography system images neurofunctional activity of the motor speech area of Broca before and during stimulation. Additionally, the optical module may be attached to the right parietal bone to examine the neurofunctional activity of the general sensory area before and during stimulation of pain, hot or cold sensation, or vibrational sensation on the left extremities, and vice versa.

Alternatively, the stimulation unit is constructed to induce physiologic and pathologic reflexes in the cerebral or spinal tissue. The stimulation unit stimulates pupillary reflexes, corneal reflexes, oculocephalic reflexes, oculovestibular reflexes, deep tendon reflexes, abdominal reflex, cremasteric reflexes, postural reflexes, gag reflex, infantile reflexes (such as blinking reflex, cochleopalpebral reflex, palmar grasp reflex, digital response reflex, rooting reflex, Galant's reflex, tonic neck reflex, Perez reflex, startle reflex).

The stimulator stimulates a selected region of the nervous system. The corresponding neurologic impulses, transmitted by the neurons, are detected and imaged at different points of their paths, for example, in the nerves, in the spinal cord, in the thalamus, or in the cerebral cortex. For example, when the stimulator causes a cold or hot stimulation on the little finger of the left hand, this thermal stimulation produces impulses that travel in the right lateral spinothalamic tract of the cervical spinal cord, to the thalamic sensory nuclei and end in the right postcentral gyrus of the parietal lobe.

In a clinical study, provided here only for illustration purposes, the optical tomography system was used to image the cognitive activity in the prefrontal cortex of a subject. High school students together with teachers and three University of Pennsylvania undergraduate mentors underwent a study using 50 MHZ phased array imaging system 15, shown in FIG. 3, to explore the repeatability of their cognitive responses and their geometric distribution on the forehead. A large number of cognitive tests were studied by selected groups of four. The simplicity and versatility of the backwards spelling was selected by the student group. Thus, each member of the team was tested by the other members for three to four episodes of rest (30 sec). The students spelled five letter words backwards (usually 5) for 30 sec, then rested for 30 sec, etc. Each time a new word was used from a word list unknown to the subject. The subject was not scored on the correctness of their response, and as soon as one spelling had been achieved, another word was given, no prompting was involved in the protocol.

The total population studied exceeded 18 participants, but as shown here the prefrontal data are highly individualized and not suitable for global averaging. Instead, for individual subjects, extensive longitudinal studies made in 20 days with 125 tests of 5 subjects were completed, and the results displayed here are based on ~25 studies of each of the five and ~50 more tests were conducted on the remaining 14 students. There was no selection of subjects in this study The back-projection images were processed using Matlab software to produce the phase and amplitude images. The phase image was robust and unambiguous. The data presentations are in the form of histogram displays of dated data accumulated over six weeks. The blood volume responses were scored by their position on the forehead, being divided up into nine areas of a 4 cm$^2$ area. Responses >20° in the particular areas were used to create histograms shown below, indicating the frequency of responses in particular areas for particular individuals. These voxels could contain at least one and possibly two responses in view of our ~1 cm$^2$ resolution. However, choice of nine areas seems adequate at present.

Brain Studies; Parietal Region

FIGS. 10A and 10B show an experimental optical image obtained by the imaging system of FIG. 3 with contralateral, parietal finger touching as a stimulation. These figures illustrate the resolution obtainable with contralateral, parietal finger touching as a stimulation. The more intense part of the image is 1.5 by 0.7 cm. The intensity is profiled on the right hand side of the figure, and the peak is approximately 4 mm in diameter. Importantly, the phase scale indicates over 40° phase shift for the peak of the parietal stimulation with a noise background of less than a few degrees of phase, confirming the very high signal to noise ratio of the phase cancellation system shown in FIGS. 3 through 5. Independent recordings of the amplitude changes measure the absorbance increase in the focal region, which is due to increased blood concentration. This wavelength will also register changes of hemoglobin oxygenation, which may accompany the blood concentration increase. Thus, the phase shift signal is a composite of increased absorbance due to blood concentration increase and a smaller decrease of absorbance due to replacement of deoxygenated blood by more oxygenated blood, the net change being increased absorbance and a shortening of the optical pathlength or phase delay.

Figure 11:
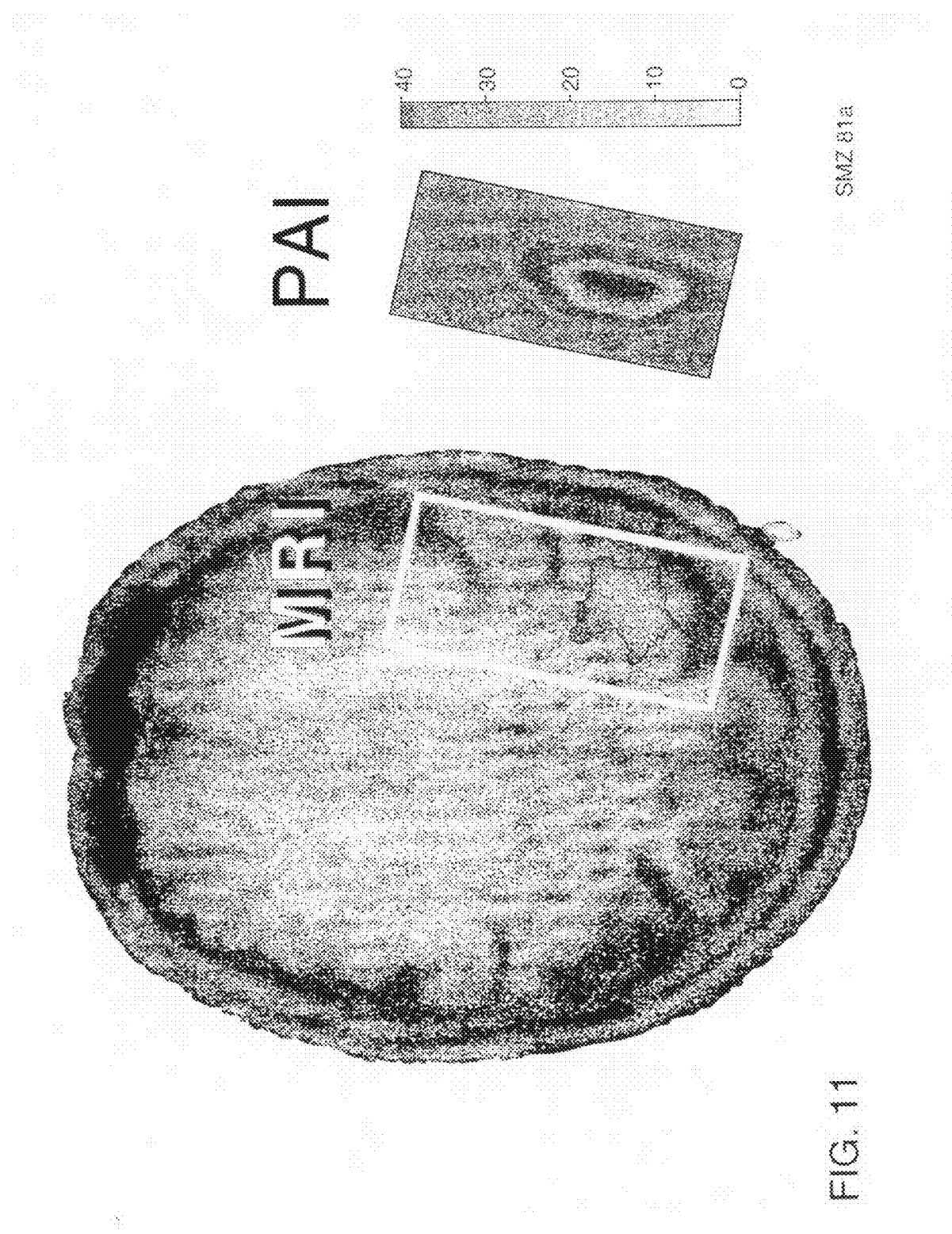
FIG. 11 shows co-registration of optical and NMR signals in sensory motor simulation.

FIG. 11. shows co-registration of optical and NMR signals in sensory motor simulation. The ability to co-register the optical images (PAI) and the MRI images is within the accuracy of the optical method for the blood volume or oxygenation changes. Thus, the maximal blood concentration increase as measured by the phased array images is congruent with maximal decrease of deoxyhemoglobin as measured by the fMRI (FIG. 11). However, the shape is elliptical rather than rectangular, 2 cm×1 cm. Such differences may be verified in future studies in which the fractional deoxygenation of hemoglobin and the blood concentration are observed rather than the incremental change of deoxyhemoglobin.

FIGS. 12A through 13D show images detected by the above described cognitive study performed by high school students, wherein the optical tomography system was used to image the cognitive activity in the prefrontal cortex of a subject. The nine source, 4 detector system operating at 780 nm on a 9cm×4 cm optical pad was located between the eyebrow and the hair line. The optical data was detected while the subject was performing backward spelling and at rest. Referring to FIGS. 13A through 13D, a second subject (KW) showed image on the other side of midline, 1.5×1 cm of varying intensity, and in the fourth repetition, a facing out of the pattern and an emergence of a pattern similar to that of the first subject. Referring to FIGS. 12A, 12B and 12C, the responses of one subject (DIPTI) to repeated tests are almost identical in position and in intensity, roughly a 1.5×3 cm area along the forehead.

FIGS. 14A and 14B are histograms of the positions on the forehead for the two subjects DIPTI and KW, respectively. Variability in response was observed, particularly in the younger members of the group who showed changes of position of the response maximum. For this reason it was considered that histograms of the position of the response on the forehead would be a better representation of the individual responses. Signals above 200 were selected and their positions were scored in nine spaces (FIG. 5) which are abbreviated, bottom right (BR), lower left (LL), center right (CR), upper middle (UM), etc. Referring to FIGS. 14A and 14B, the two individuals exhibit different portions of the prefrontal cortex in responding to the task of spelling backwards. FIG. 14A employs mainly the center left region, and the upper middle region to a small extent. FIG. 14B exhibits the upper middle region to a much greater extent than the center left region. These two cases are exemplary of the many subjects studied, and define what may be a novel and important element of pre-frontal cognitive response. Note that both subjects nearly always responded in the dominant position over the four test intervals.

Neonates Imaging

Figures 15A, 15B:
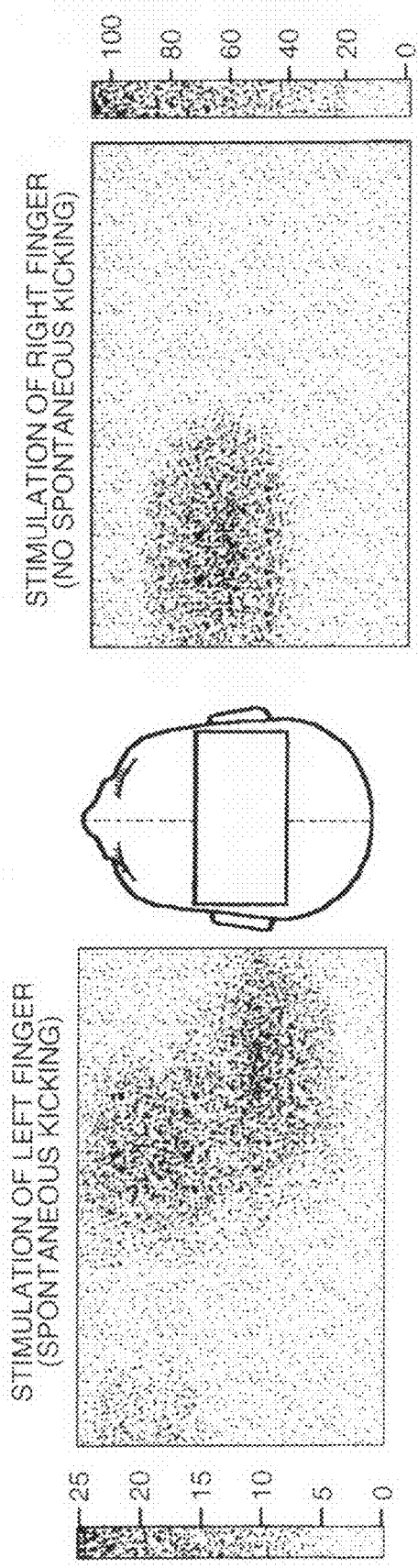
FIGS. 15A and 15B show optical images during the functional activation of pre- and full-term neonates.

In another clinical study, provided here for illustration only, this technique has been applied to the functional activation of pre- and full-term, non-white neonates as shown in FIGS. 15A and 15B. In this case, prefrontal activity could not yet be tested, instead, the sensorimotor region was tested. The probe was held on the head of the infant for 30 sec to acquire a rest image. Touching the right finger evokes a response imaged over 30 sec. The magnitude is large; a 100° phase shift and an image approximately 2 cm in size in the contralateral hemisphere is indicated. When, however, the right finger is touched, a similar area of response is obtained in the contralateral hemisphere displaced laterally. In addition, the right leg kicked spontaneously.

The examined infant was a 26 week gestation, 1 kilogram, premature infant, which was studied at age four weeks. The stimulation, in this case, was touching the baby's right finger (FIG. 15B). A distinct image was obtained somewhat on the contralateral side (approximately 1×1.5 cm in size), and of a large magnitude (over 100° phase shift). Stimulation of the left finger (FIG. 15B A) gave a distinctive image of the same size but laterally displaced in the right hemisphere. At the same time, the spontaneous kicking was clearly resolved and the image was displaced laterally. Thus, images of the voluntary and involuntary responses of the pre-term neonate brain were obtained.

While these data are preliminary, they are remarkable for the large amplitude of the responses, in fact as large as observed in the high school student population. This large response of the neonates as compared with the high school population is due to in part to their thinner skull and smaller CSF space. This works well for the detection of diminished response of dysfunctional infants who may have had hypoxia/ischemia or other traumatic events either pre-partum or intrapartum.

The formation of a well resolved image of brain function using multiple light sources and detectors in the NIR region, with either continuous or modulated light, opens up a fertile field of study of visual sensorimotor and prefrontal functions in adults, full- and pre-term neonates. The methods are intentionally over-simplified to afford a fast, simple, straight-forward, safe and affordable method for studying brain function. Sufficient studies of the high school students were made to ensure validity of the stability of the signal and of the position of the maximal response for a given individual and of the variability of the response among individuals. The striking results are the plasticity of the response of the pre-frontal area observed in the series of the high school student studies on the one hand, and ease with which evoked signals in the parietal region are obtained with the pre- and full-term infant on the other. Thus, we present a preliminary report on these studies in order to stimulate further research, here and elsewhere.

These results make practical and affordable for large populations the complex technology of measuring brain function. While lacking the resolution of MRI or the chemical specificity of PET, it has the capability of multi-wavelength operation to give enhanced sensitivity for oxy-, deoxy-hemoglobin and for light scattering changes. More importantly, the method opens-up new fields of study of the human population, in adults under conditions of simulated or real stress that may have important effects upon functional performance, or in other cases, where the subject cannot be well controlled as in the full- and pre-term neonate and those not fully responsive due to accidents or due to disease.

Higher Resolution Images

In previous studies, optical tomography has attempted to mimic the X-ray image by a 2D projection of absorbance usually in 2 planes. The success of this techniques is based upon the ability of the radiologist to identify the structures of either scattering or absorbing material that differ from the normal tissue. However, a high resolution is required to delineate such structural features on which identification of malignant tissue is usually based. High resolution is time intensive as well as apparatus intensive, i.e., numerous source detector combinations are required to achieve resolution comparable to PET/MRI. In the above systems, imaging resolution is employed mainly to increase the signal to noise ratio in quantifying optical properties of the tumor with respect to normal tissue or a model of a normal tissue. However, the blood volume, oxygenation and deoxygenation data collected by the optical systems do not depend critically upon high resolution imaging.

An optical system with an increased number of sources and detectors will render higher spatial resolution. Furthermore, a larger source-detector separation (i.e., the input port to detection port separation) achieves deeper penetration of the introduced optical radiation. By using selected separation values, the above-described imaging systems can collect three-dimensional optical data that are used for three dimensional reconstruction.

Additional embodiments are within the following claims.

The invention claimed is:

1. An optical system for in vivo, non-invasive transcranial examination of brain tissue of a subject comprising:
    at least one light source constructed to emit visible or infrared light, and at least one light detector;
    an optical module including an array of optical input ports and detection ports located in a geometrical pattern to provide a multiplicity of photon migration paths inside an examined region of brain tissue, said optical input ports being constructed to introduce visible or infrared light emitted from said at least one light source, said optical detection ports being constructed to receive photons of light that have migrated in the examined tissue region from at least one of said input ports and provide said received light to said at least one light detector;
    a controller constructed and arranged to control operation of said at least one light source and said at least one light detector to detect light that has migrated over at least one of said photon migration paths; and
    a processor connected to receive signals from said at least one light detector and programmed to form at least two data sets, wherein each data value corresponds to said detected light for a pair of said input and said detection ports, a first of said data sets representing blood volume in the examined tissue region and a second of said data sets representing blood oxygenation in the examined tissue region; said processor being programmed to calculate spatial congruence of said first and second data sets by calculating a difference between said blood volume and oxygenation data divided by a normalized value to detect abnormal tissue in the examined tissue region of the brain tissue.

2. The optical system of claim 1 wherein said processor is programmed to form said second data set that includes hemoglobin deoxygenation values.

3. The optical system of claim 1 wherein said processor is programmed to form a third data set being collected by irradiating a reference tissue region.

4. The optical system of claim 1 further including a second optical module including a second-mentioned array of optical input ports and detection ports located in a selected geometrical pattern to provide a multiplicity of photon migration paths inside an examined region of the tissue, said optical input ports of said second-mentioned array being constructed to introduce visible or infrared light emitted from said at least one light source, said optical detection ports of said second-mentioned array being constructed to receive photons of light that have migrated in the examined tissue region from at least one of said input ports and provide said received light to said at least one light detector; said processor being arranged to receive optical data from both said optical modules.

5. The optical system of claim 1 wherein said processor is programmed to determine said congruence using a formula:

$$1\left(\frac{\text{maximum overlap residual}}{\text{maximum selected tissue signal}}\right) \times 100.$$

6. The optical system of claim 1 wherein said processor is further programmed to determine a location of said abnormal tissue within the examined tissue region.

7. The optical system of claim 1 wherein said processor is programmed to produce from at least one of said data sets an image data set by implementing an optical tomography algorithm.

8. The optical system of claim 7 in which said optical tomography algorithm employs factors related to determined probability distribution of photons attributable to the scattering character of the tissue being imaged.

9. The optical system of claim 7 further including a display device constructed to receive said image data set from said processor and to display an image.

10. The optical system of claim 1 wherein said controller is constructed and arranged to activate said at least one light source and said at least one light detector to obtain a first selected distance between said input and detection ports and said processor is programmed to form said data sets for said first distance.

11. The optical system of claim 10 wherein said processor is programmed to produce an image data set from at least one of said data sets formed for said first distance.

12. The optical system of claim 10 wherein said controller is further constructed and arranged to activate said at least one light source and said at least one light detector to obtain second distance between said input and detection ports and said processor is programmed to form said data sets for said second distance.

13. The optical system of claim 1 further comprising
    a first oscillator constructed to generate a first carrier waveform at a first frequency on the order of $10^8$ Hz, said first frequency having a time characteristic compatible with the time delay of photon migration from said input port to said detection port;
    said at least one light source being coupled to said first oscillator and constructed to generate said light modulated by said first carrier waveform;
    a phase detector constructed to determine change in waveform of the detected light relative to the waveform of the introduced light and measure therefrom the phase shift of said detected light at said wavelength, said phase-shifted light being indicative of scattering or absorptive properties of the examined tissue region; and said processor being programmed to form said data sets based on the measured phase shift.

14. The optical system of claim 13 further comprising a second oscillator constructed to generate a second waveform at a second frequency;

said at least one light detector being arranged to receive a reference waveform at a reference frequency offset by a frequency on the order of $10^3$ Hz from said first frequency and to produce a signal, at said offset frequency, corresponding to said detected radiation; and said phase detector being adapted to compare, at said offset frequency, the detected radiation with the introduced radiation and to determine therefrom said phase shift.

15. The optical system of claim 1 further comprising:

an oscillator constructed to generate a first carrier waveform of a selected frequency compatible with time delay of photon migration from said input port to said detection port; said at least one light source being connected to receive from said oscillator said carrier waveform and constructed to generate optical radiation modulated at said frequency;

a phase splitter connected to receive said carrier waveform from said oscillator and produce first and second reference phase signals of predefined substantially different phases;

first and second double balanced mixers connected to receive from said phase splitter said first and second reference phase signals, respectively, and connected to receive from said at least one light detector said detector signal and to produce therefrom a in-phase output signal and a quadrature output signal, respectively; and said processor being connected to said double balanced mixers and arranged to receive said in-phase output signal and said quadrature output signal and programmed to form therefrom said data sets.

16. The optical system of claim 15 wherein said processor is programmed to calculate a phase shift ($\Theta_\lambda$) between said light introduced at said input port and said light detected at said detection port prior to forming said data sets.

17. The optical system of claim 15 wherein said processor is programmed to calculate an average migration pathlength of photons scattered in the examined tissue between said optical input port and said optical detection port prior to forming said data sets.

18. The optical system of claim 17 wherein said processor further employs said pathlength in quantifying hemoglobin saturation (Y) of the examined tissue.

19. The optical system of claim 15 wherein said processor is programmed to calculate a signal amplitude ($A_\lambda$) determined as a square root of a sum of squares of said in-phase output signal and said quadrature output signal prior to forming said data sets.

20. The optical system of claim 19 further comprising:

a narrow band detector connected to receive from said at least one light detector said detector signal and to produce a DC output signal therefrom; and said signal processor further determining a modulation index ($M_\lambda$) as a ratio of values of said signal amplitude and said signal amplitude plus said DC output signal.

21. The optical system of claim 1 further comprising:

at least one oscillator constructed to generate a carrier waveform of a selected frequency, said at least one light source being operatively connected to said oscillator constructed to generate light of a visible or infrared wavelength, said light being intensity modulated at said frequency to achieve a known light pattern;

said controller constructed to control the emitted light intensity or phase relationship of patterns simultaneously introduced from multiple input ports, said introduced patterns forming resulting radiation that possesses a substantial gradient of photon density in at least one direction, said resulting radiation being scattered and absorbed over said migration paths;

said at least one light detector constructed and arranged to detect over time the resulting radiation that has migrated in the tissue to said detection port, and said processor being further programmed to process signals of said detected resulting radiation in relation to said introduced radiation to create said data sets indicative of influence of the examined tissue upon said substantial gradient of photon density of said resulting radiation.

22. The optical system of claim 21 further comprising a phase detector constructed to detect the phase of the detected radiation and provide said phase to said processor.

23. The optical system of claim 21 further comprising an amplitude detector constructed to detect the amplitude of the detected radiation and provide said amplitude to said processor.

24. The optical system of claim 21 wherein the phase relationship of light patterns introduced from two input ports is 180 degrees.

25. The optical system of claim 1 wherein said at least one light source produces relatively long light pulses and the processor is programmed to form said data sets by subtracting amplitude of two said pulses emitted from two input ports located symmetrically relative to one detection port.

26. The optical system of claim 1, wherein said at least one light source is constructed to introduce photons of two wavelengths selected to provide sensitivity to a tissue constituent.

27. The optical system of claim 1 wherein said at least one light source is constructed to introduce photons of two wavelengths providing sensitivity to a tissue constituent being an endogenous pigment.

28. The optical system of claim 1 wherein said at least one light source is constructed to introduce photons of two wavelengths providing sensitivity to an endogenous pigment including hemoglobin.

29. The optical system of claim 1 wherein said at least one light source is constructed to introduce photons of two wavelengths providing sensitivity to a tissue constituent including an exogenous pigment.

30. The optical system of claim 1 wherein said at least one light source is constructed to introduce photons of two wavelengths providing sensitivity to an exogenous pigment including a selected contrast agent.

31. The optical system of claim 1, wherein said geometrical pattern includes for one said input port several detection ports equally spaced apart from said one input port.

32. The optical system of claim 1, wherein said geometrical pattern includes for one said detection port several input ports equally spaced apart from said one detection port.

33. An optical method for in vivo, non-invasive transcranial examination of brain tissue of a subject comprising:

providing an optical module including an array of optical input ports and detection ports located in a geometrical pattern to provide a multiplicity of photon migration paths inside an examined region of brain tissue;

placing said optical module on the exterior of the head of the subject;

introducing visible or infrared light from at least one said optical input port into the examined tissue region and receiving photons of light that have migrated in the examined tissue region to at least one of said detection ports;

detecting said received photons by at least one light detector optically coupled to at least one said detection port;

controlling said introducing and detecting steps to collect optical data corresponding to photons of light that have migrated between selected input and detection ports;

processing said optical data to form at least two data sets, a first of said data sets representing blood volume in the examined tissue region and a second of said data sets representing blood oxygenation in the examined tissue region; and correlating said first and second data sets by calculating spatial congruence between said blood volume and oxygenation data sets by calculating a difference between said blood volume and oxygenation data divided by a normalized value to detect abnormal tissue in the examined tissue region of the brain tissue.

34. The optical method of claim 33 including ordering said first and second data sets as two-dimensional images and determining said congruence using said two-dimensional images.

35. The optical method of claim 33 including ordering said first and second data sets as two-dimensional images and determining said congruence using a formula:

$$1\left(\frac{\text{maximum overlap residual}}{\text{maximum selected tissue signal}}\right) \times 100.$$

36. The optical method of claim 33 including determining a location of said abnormal tissue within the examined tissue region.

37. The optical method of claim 33 including producing from at least one of said data sets an image data set by implementing an optical tomography algorithm.

* * * * *